US010328261B2

United States Patent
Glasser

(10) Patent No.: US 10,328,261 B2
(45) Date of Patent: Jun. 25, 2019

(54) ACCOMMODATION STIMULATION AND RECORDING DEVICE

(71) Applicant: UNIVERSITY OF HOUSTON SYSTEM, Houston, TX (US)

(72) Inventor: Adrian Glasser, Bellaire, TX (US)

(73) Assignee: UNIVERSITY OF HOUSTON SYSTEM, Houston, TX (US)

(*) Notice: Subject to any disclaimer, the term of this patent is extended or adjusted under 35 U.S.C. 154(b) by 214 days.

(21) Appl. No.: 15/398,491

(22) Filed: Jan. 4, 2017

(65) Prior Publication Data

US 2017/0113043 A1    Apr. 27, 2017

Related U.S. Application Data

(62) Division of application No. 14/298,203, filed on Jun. 6, 2014.

(Continued)

(51) Int. Cl.
*A61N 1/36* (2006.01)
*A61B 3/11* (2006.01)
(Continued)

(52) U.S. Cl.
CPC .......... *A61N 1/36046* (2013.01); *A61B 3/112* (2013.01); *A61B 5/0496* (2013.01);
(Continued)

(58) Field of Classification Search
CPC .. A61N 1/0404; A61N 1/0452; A61N 1/0543; A61N 1/36003; A61N 1/36046; A61B 5/6821
See application file for complete search history.

(56) References Cited

U.S. PATENT DOCUMENTS 4,603,697 A    8/1986 Kamerling
5,782,894 A    7/1998 Israel
(Continued)

OTHER PUBLICATIONS

Burian et al. "A speculum contact lens electrode for electroretinography". Electroencephalography and Clinical Neurophysiology vol. 6, 1954, pp. 509-511.*

(Continued)

*Primary Examiner* — Eugene T Wu
(74) *Attorney, Agent, or Firm* — Carter, DeLuca & Farrell LLP; George Likourezos, Esq.

(57) ABSTRACT

Embodiments described herein generally relate to devices and methods for stimulation or recording of accommodation of an eye. Accommodation of an eye naturally occurs through contraction of the ciliary muscle. Embodiments described herein can deliver electrostimulation to the ciliary muscle through a pair of electrodes which deliver power over an area of the sclera which is both positioned above and over an area which is substantially equivalent to the surface area of the ciliary muscle. In further embodiments, electrical impulses produced by the ciliary muscle can be received by one or more electrodes positioned proximate the ciliary muscle. Thus, by embodiments described herein, accommodation of the eye can be reproducibly achieved by external stimulation of the ciliary muscle or measured based on electrical impulses generated by or in conjunction with the ciliary muscle.

6 Claims, 28 Drawing Sheets

Related U.S. Application Data

(60) Provisional application No. 61/834,921, filed on Jun. 14, 2013.

(51) Int. Cl.
- *A61B 5/0496* (2006.01)
- *A61N 1/05* (2006.01)
- *A61B 5/00* (2006.01)
- *A61N 1/04* (2006.01)

(52) U.S. Cl.
CPC .......... *A61B 5/6821* (2013.01); *A61N 1/0526* (2013.01); *A61N 1/0476* (2013.01)

(56) References Cited

U.S. PATENT DOCUMENTS

| | | |
|---|---|---|
| 6,282,449 B1 | 8/2001 | Kamerling et al. |
| 9,014,812 B2 | 4/2015 | Filippello |
| 2005/0010266 A1 | 1/2005 | Bogdanowicz |
| 2006/0095108 A1 | 5/2006 | Chowdhury et al. |
| 2006/0116740 A1 | 6/2006 | Morimoto et al. |
| 2006/0136022 A1* | 6/2006 | Wong, Jr. ............... A61B 3/165 607/104 |
| 2008/0208335 A1 | 8/2008 | Blum et al. |
| 2008/0294066 A1 | 11/2008 | Hetling et al. |
| 2011/0082518 A1 | 4/2011 | Filippello |
| 2011/0184358 A1 | 7/2011 | Weiner et al. |

OTHER PUBLICATIONS

Esakowitz et al. "A comparison of flash electroretinograms recorded from Burian Allen, JET, C-glide, gold foil, DTL and skin electrodes". Eye (Lond). 1993;7 ( Pt 1):169-71.*

PCT International Search Report and Written Opinion dated Oct. 1, 2014, for International Patent Application No. PCT/US2014/041383.

Office Action for U.S. Appl. No. 14/298,203 dated Jun. 16, 2016.

Final Office Action for U.S. Appl. No. 14/298,203 dated Oct. 4, 2016.

* cited by examiner

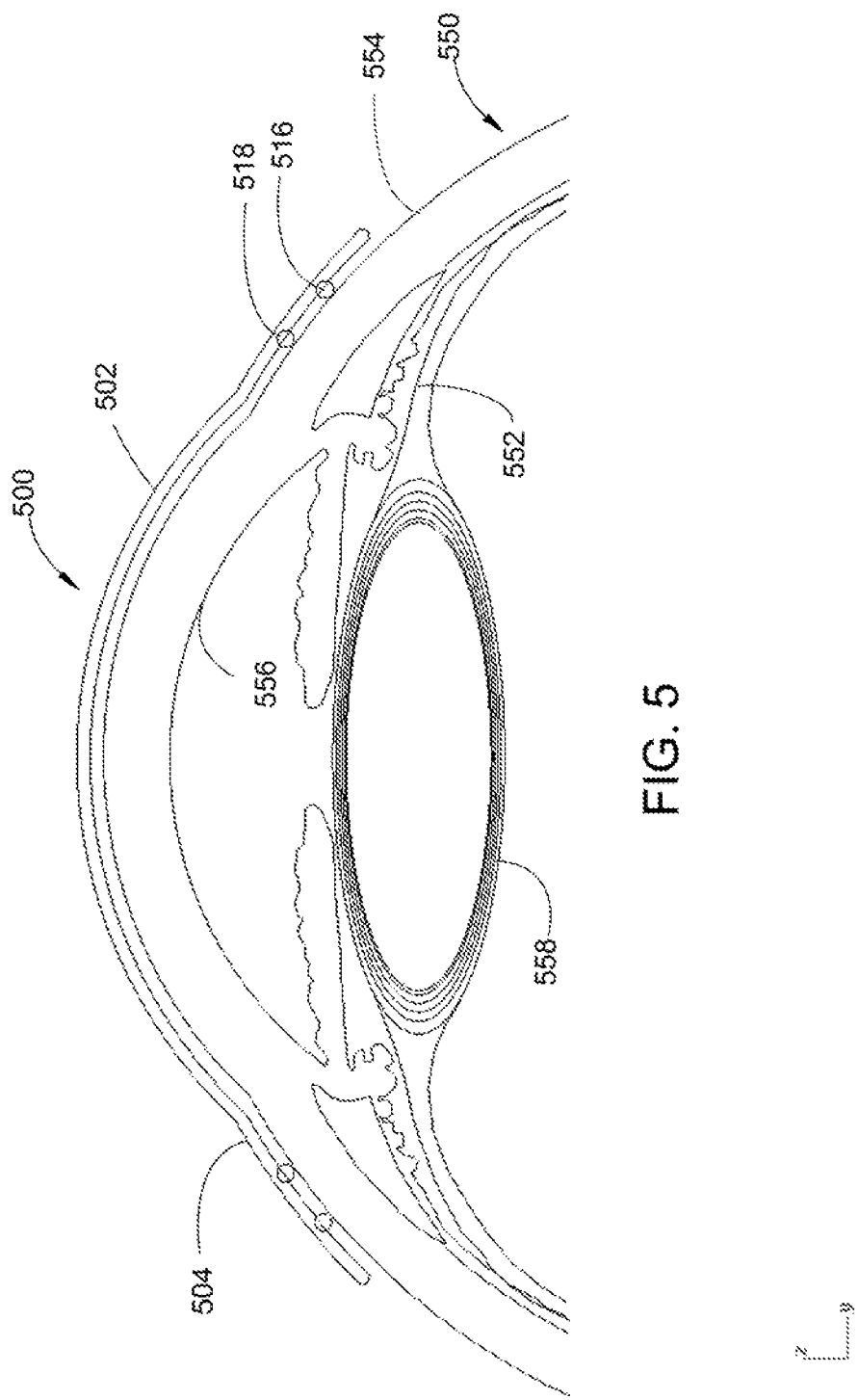

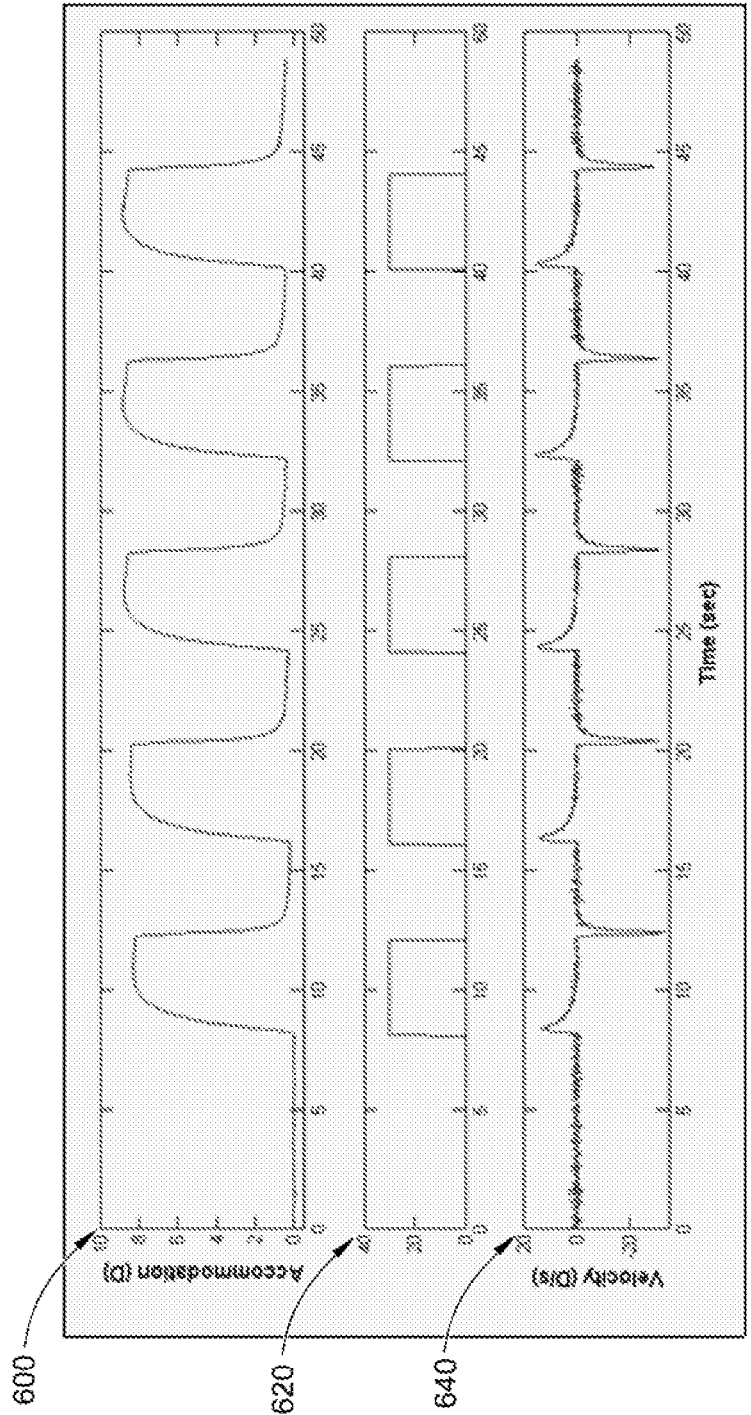

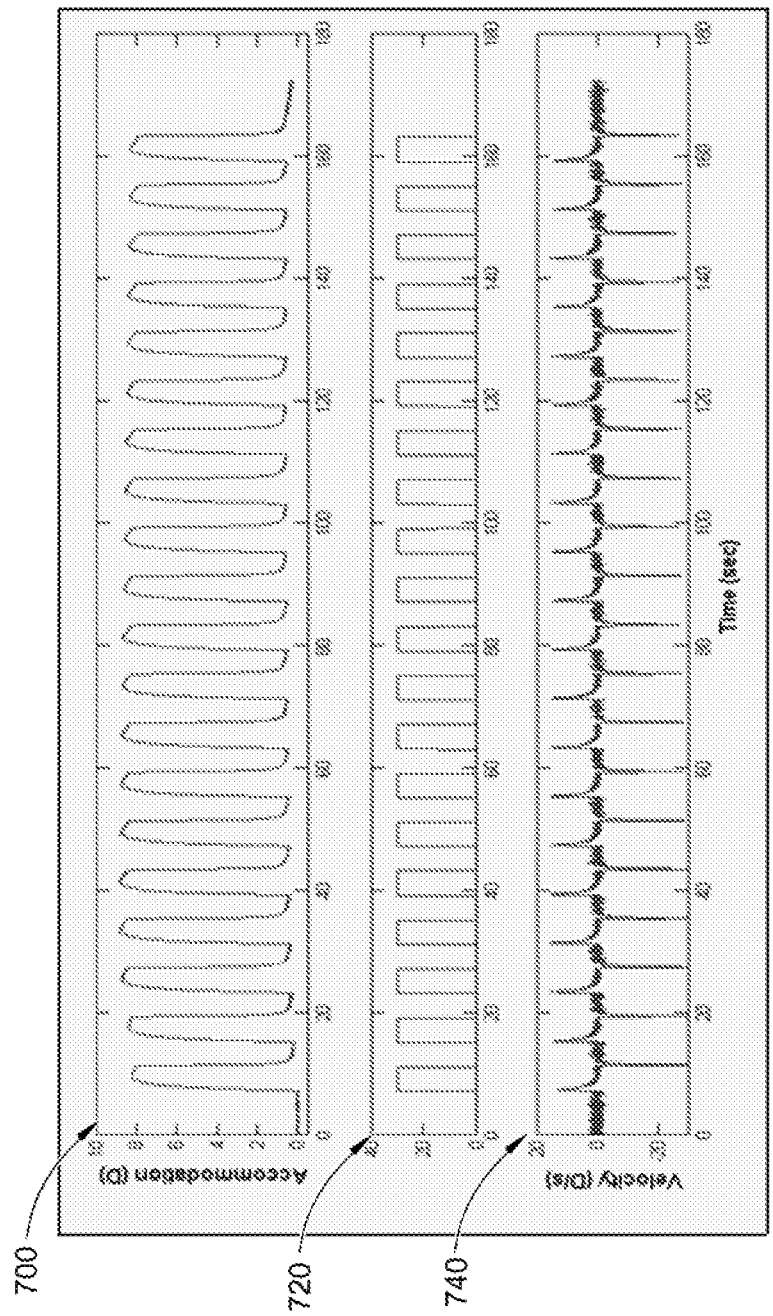

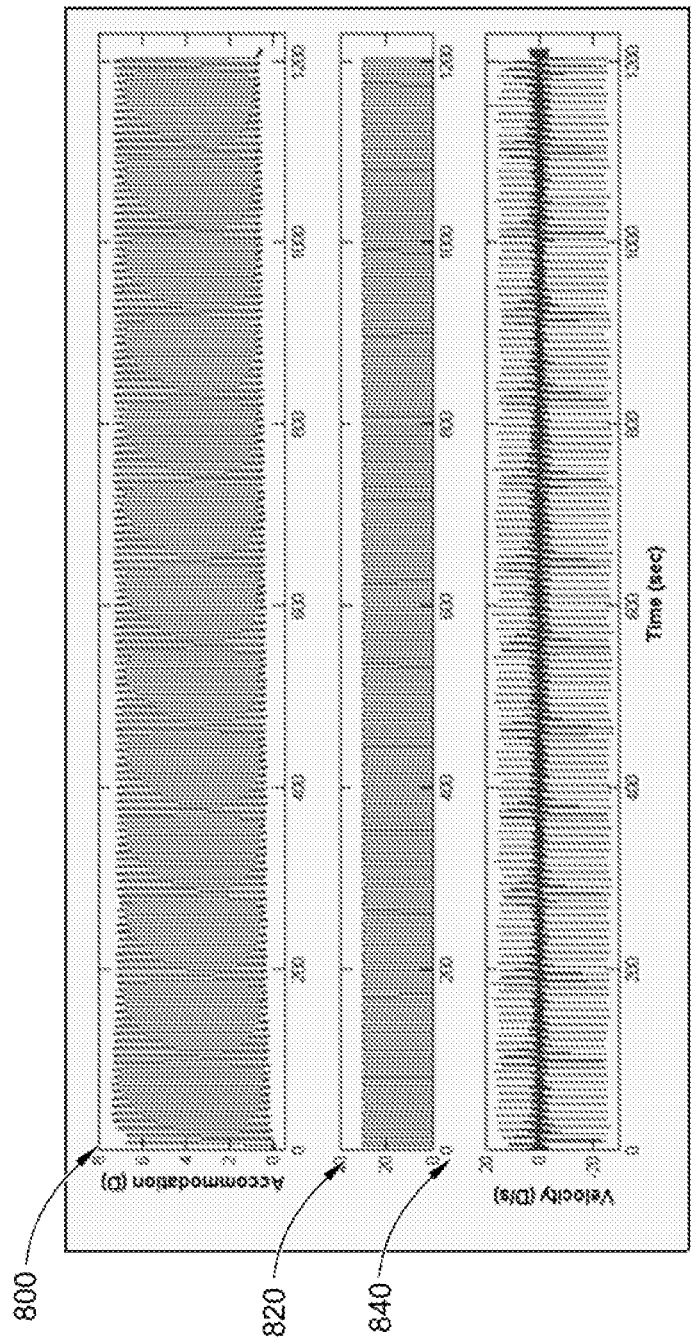

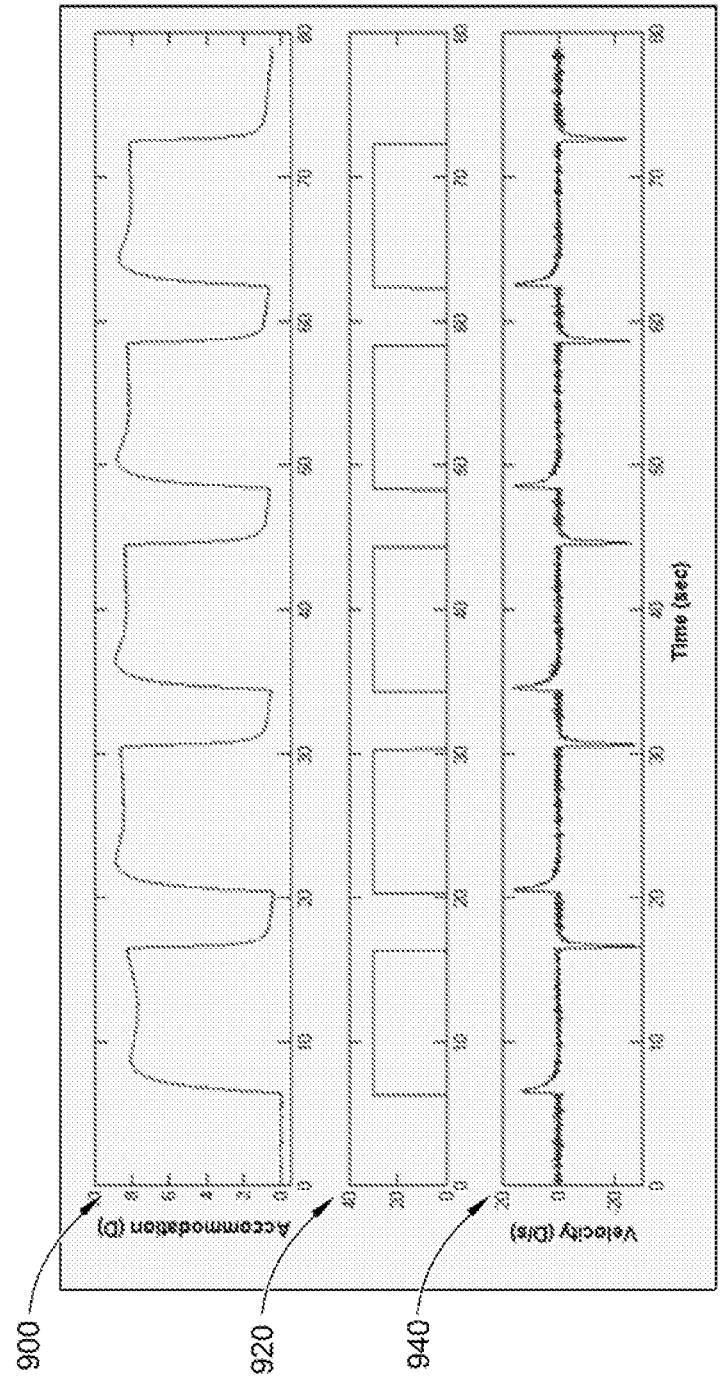

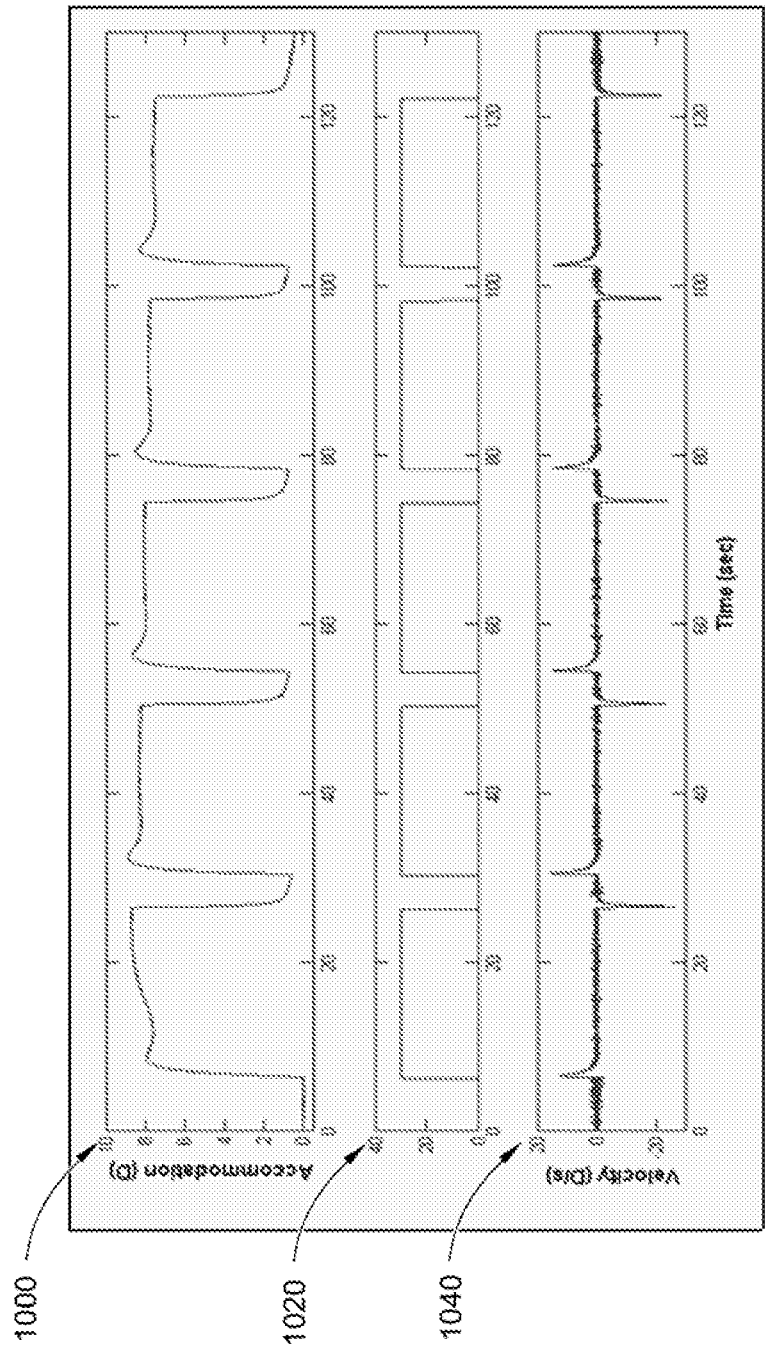

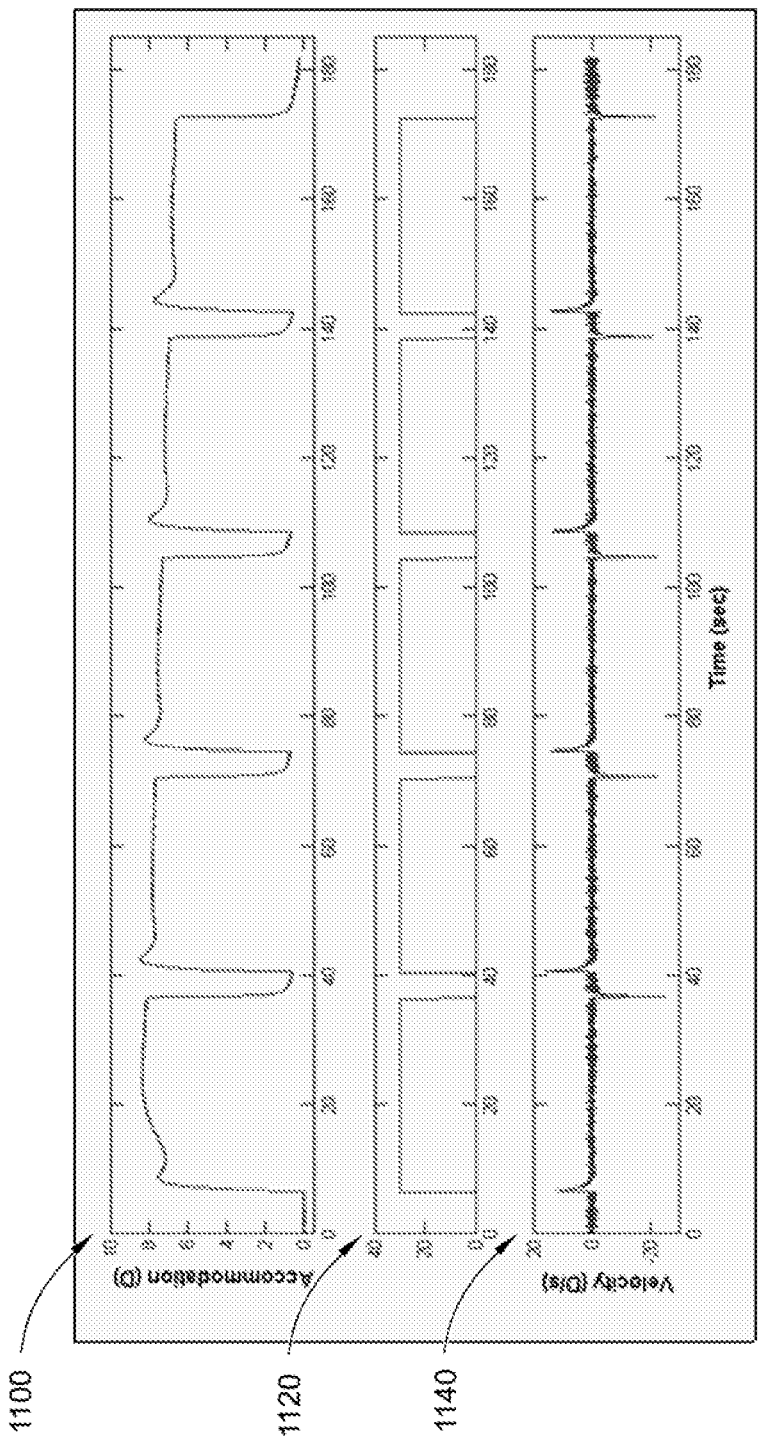

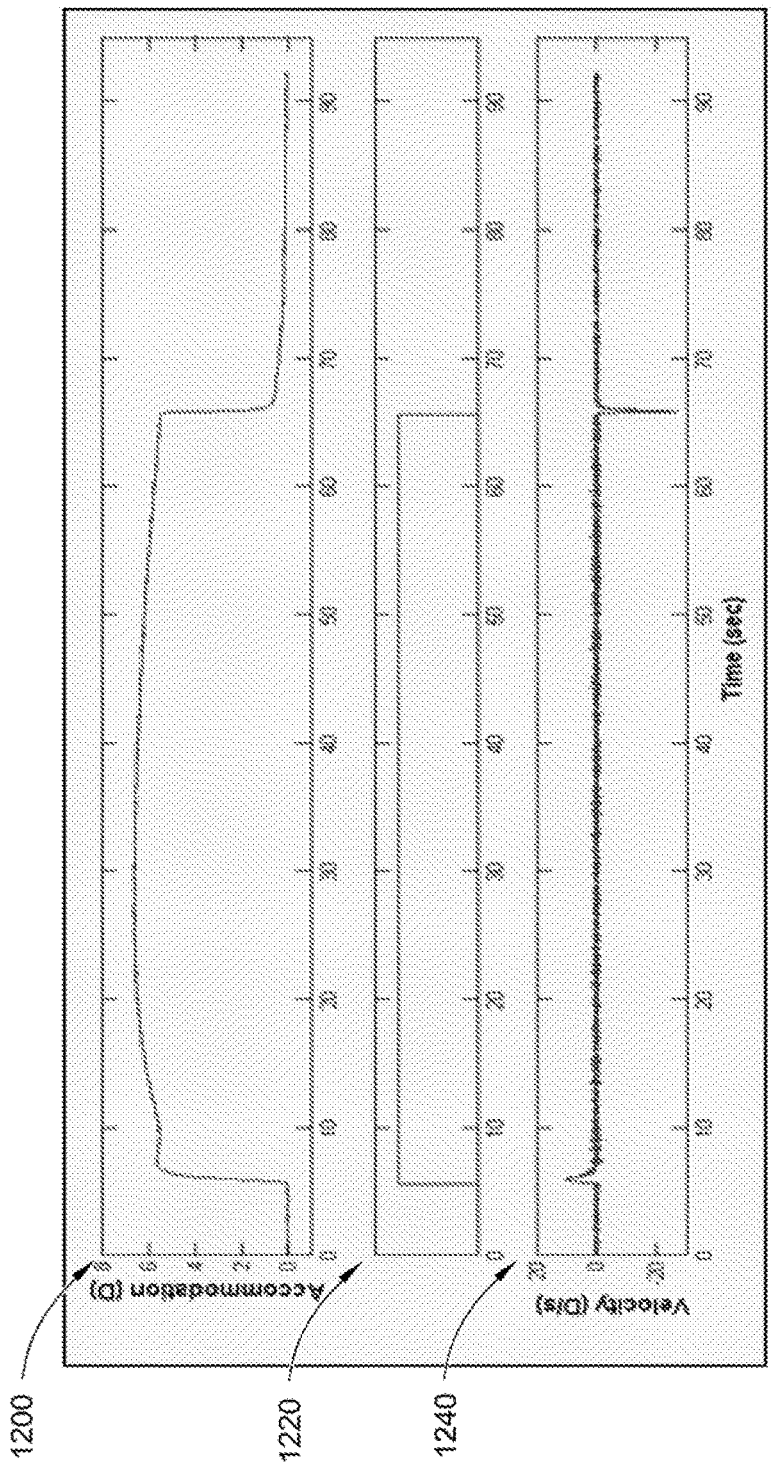

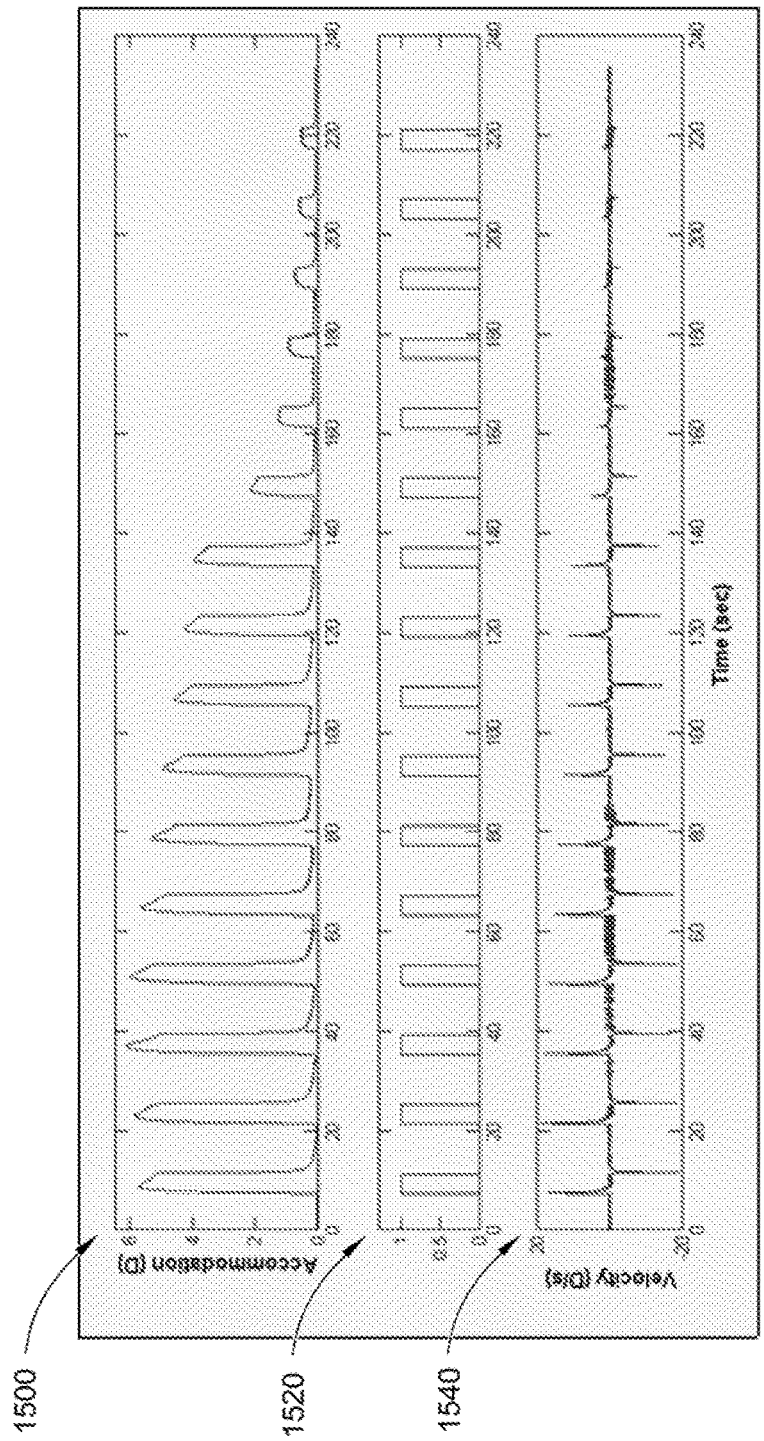

ACCOMMODATION STIMULATION AND RECORDING DEVICE

CROSS-REFERENCE TO RELATED APPLICATION

This application claims benefit of U.S. patent application Ser. No. 14/298,203, filed Jun. 6, 2014, which claims priority to U.S. Provisional Patent Application Ser. No. 61/834,921, filed Jun. 14, 2013, each of which is herein incorporated by reference in its entirety.

BACKGROUND

Field

Embodiments disclosed herein generally relate to devices and methods for manipulating and recording accommodation in the eye.

Description of the Related Art

Accommodation is the process whereby the young eye changes focus from distance to near. This occurs through a contraction of the ciliary muscle inside the eye. This ciliary muscle contraction causes the lens in the young eye to change shape, which increases the optical power of the eye. The normal accommodative response is rapid in the young eye. The young eye can change focus within about 100-200 milliseconds.

Accommodation is progressively lost with increasing age in the condition called presbyopia. Presbyopia is due to a progressive age-related increase in stiffness of the lens. In humans, accommodation can be produced by having subjects look from a distant target to near-reading text positioned progressively closer to the eyes (known as visual stimulus elicited accommodation). In visual stimulus elicited accommodation, the subject perceives the near object, perceives that the near object (in this case, text) is out of focus and attempts to make the near object clear by accommodating. In presbyopes (persons affected by presbyopia), the subject would perceive the near object is out of focus, but they would not be able to accommodate to change their focus to get the near object in clear focus.

How the eye accommodates, why this physiological function is lost with increasing age and trying to understand if accommodation can be restored in presbyopes is an area of significant basic science, clinical and industry research. Such research is undertaken on human subjects as well as on animal models including non-human primates, especially rhesus monkeys. Rhesus monkeys accommodate in a very similar fashion to the way humans do. Rhesus monkeys also develop presbyopia.

A significant challenge in this area of clinical and laboratory research is how to stimulate accommodation either in human subjects or in animal models. Stimulating accommodation can be challenging for many reasons. For example, in conscious human subjects although presenting near reading text may represent a stimulus to accommodate, the subjects may simply choose not to accommodate or they may not elicit a strong effort to accommodate. Similarly, in animal models, if the animals are anesthetized, it can be challenging to stimulate accommodation.

In both humans and animal models, accommodation can be stimulated by applying drugs, such as pilocarpine, directly to the eye. This produces an accommodative response because the drugs diffuse into the eye and cause the ciliary muscle in the eye to contract. However, drug stimulated accommodation may be very slow relative to the natural accommodative response. In some examples, the drug stimulated accommodation can take 30-45 minutes to achieve a maximum. When compared to the previously described 100-200 milliseconds for natural accommodation to occur, known drug induced accommodation techniques appear inadequate for studying natural accommodation. Further, in current drug stimulation models, the accommodation response can only be elicited a single time in each experimental session.

In animal models where a dynamic accommodative response is desired, complex, lengthy and invasive surgical procedures are required to stimulate dynamic accommodative responses with electrical stimulation. As such, the complexity and expense of the procedure, ethical concerns and danger to the animal all act to limit dynamic accommodation experimentation.

Thus, there is a need for safe and effective exogenous control of accommodation in both humans and animal models.

SUMMARY

The embodiments described herein generally relate to methods and devices for affecting or recording an accommodation response.

In one embodiment, an electrostimulation device can include a device body with a circular shape and an outer circumference, the device body comprising an anterior surface and a posterior surface, and on the posterior surface an inner ring electrode and an outer ring electrode both comprising an electrically-conductive material, the outer ring electrode, the inner ring electrode and the outer circumference of the device body forming concentric circles and an electrical stimulation source in electrical connection with the inner ring electrode and the outer ring electrode.

In another embodiment, a scleral contact lens electrode can include a device body, an inner ring electrode comprising an electrically-conductive material adapted to contact the posterior surface of the scleral contact region, an outer ring electrode comprising an electrically conductive material adapted to contact the posterior surface of the scleral contact region and circumscribing the inner ring electrode and an electrical stimulation source in electrical connection with the inner ring electrode and the outer ring electrode. The device body can include a transparent lens with a posterior surface and an anterior surface, the posterior surface adapted to contact the cornea and the scleral contact region, the scleral contact region circumscribing the transparent lens.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 5 depicts an accommodation stimulation scleral contact lens adapted to contact an eye according to an embodiment;

FIGS. 6A-6C are graphical depictions of measurements related to accommodative responses created by an accommodation stimulation device according to an embodiment;

FIGS. 7A-7C depict a plurality of stimulated accommodative responses using the accommodation stimulation device according to an embodiment;

FIGS. 8A-8D depict a plurality of stimulated accommodative responses using an accommodation stimulation device according to an embodiment;

FIGS. 9A-9C depict a plurality of stimulated accommodative responses using an accommodation stimulation device according to an embodiment;

FIGS. 10A-10C depict a plurality of stimulated accommodative responses using an accommodation stimulation device according to an embodiment;

FIGS. 11A-11C depict a plurality of stimulated accommodative responses using an accommodation stimulation device according to an embodiment;

FIGS. 12A-12C depict a single extended stimulated accommodative response using an accommodation stimulation device according to an embodiment;

FIGS. 15A-15C depict a plurality of stimulated accommodative responses with progressively decreasing frequencies using an accommodation stimulation device according to an embodiment;

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Embodiments disclosed herein generally relate to devices that can be placed on the eye to electrically stimulate accommodation or to record the electrical activity of the ciliary muscle when it contracts during an accommodative effort and methods for exogenous accommodation in human subjects or in animals, including monkeys.

The accommodation stimulation devices can stimulate accommodation without requiring any participation from the subject to elicit an accommodative response. Accommodation can be achieved through the embodiments described herein in a non-invasive fashion. The accommodation stimulation devices described herein can produce a rapidly occurring accommodative response, such as in the order of milliseconds, and can elicit many repeated accommodative responses. Further in the accommodation stimulation devices described herein, the frequency, duration and amplitude of the accommodative responses can be regulated by controlling the stimulus characteristics. The embodiments disclosed herein are more clearly described with reference to the figures below.

Accommodation Stimulation Speculum

In one embodiment, an accommodation stimulation speculum is provided to achieve accommodation. As used herein, the accommodation stimulation speculum is a device to hold the eyelids open while delivering electrostimulation to the ciliary muscle. The accommodation stimulation speculum positions a plurality of ring electrodes adapted to contact the sclera over the area of the ciliary muscle. The accommodation stimulation speculum is therefore capable of delivering electrostimulation in a non-invasive fashion in either conscious or sedated subjects.

Figure 1A:
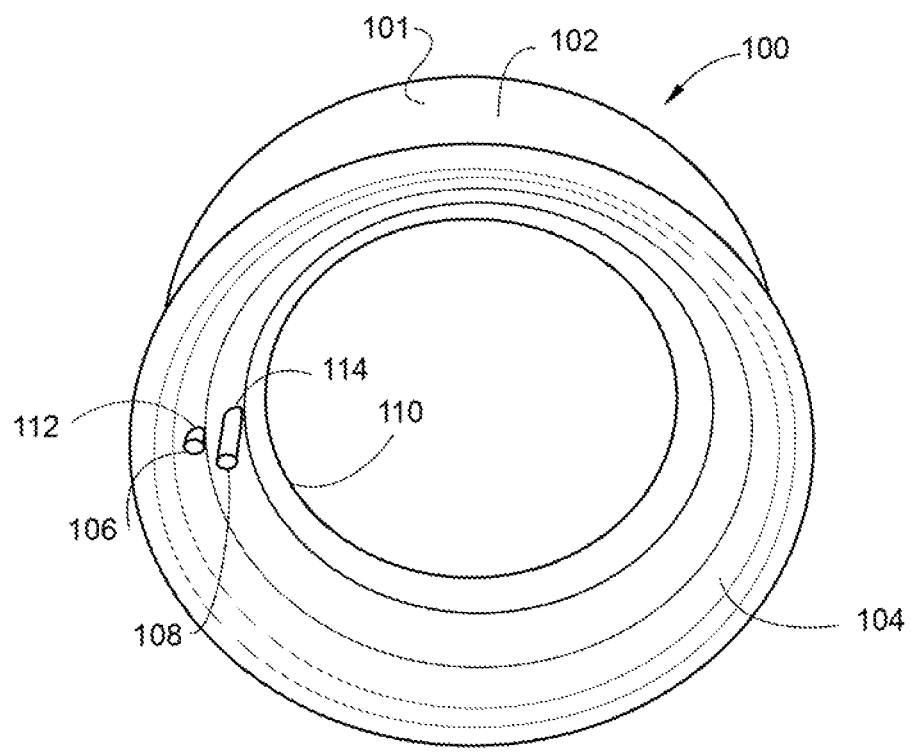
FIG. 1A depicts a frontal view of an accommodation stimulation speculum according to an embodiment.
Figure 1B:
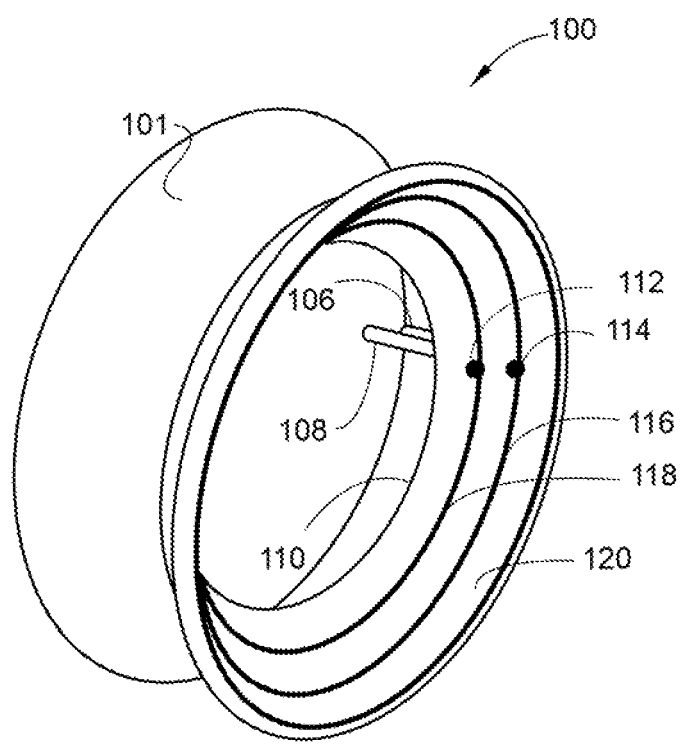
FIG. 1B depicts a rear view of the accommodation stimulation speculum according to an embodiment.
Figure 1C:
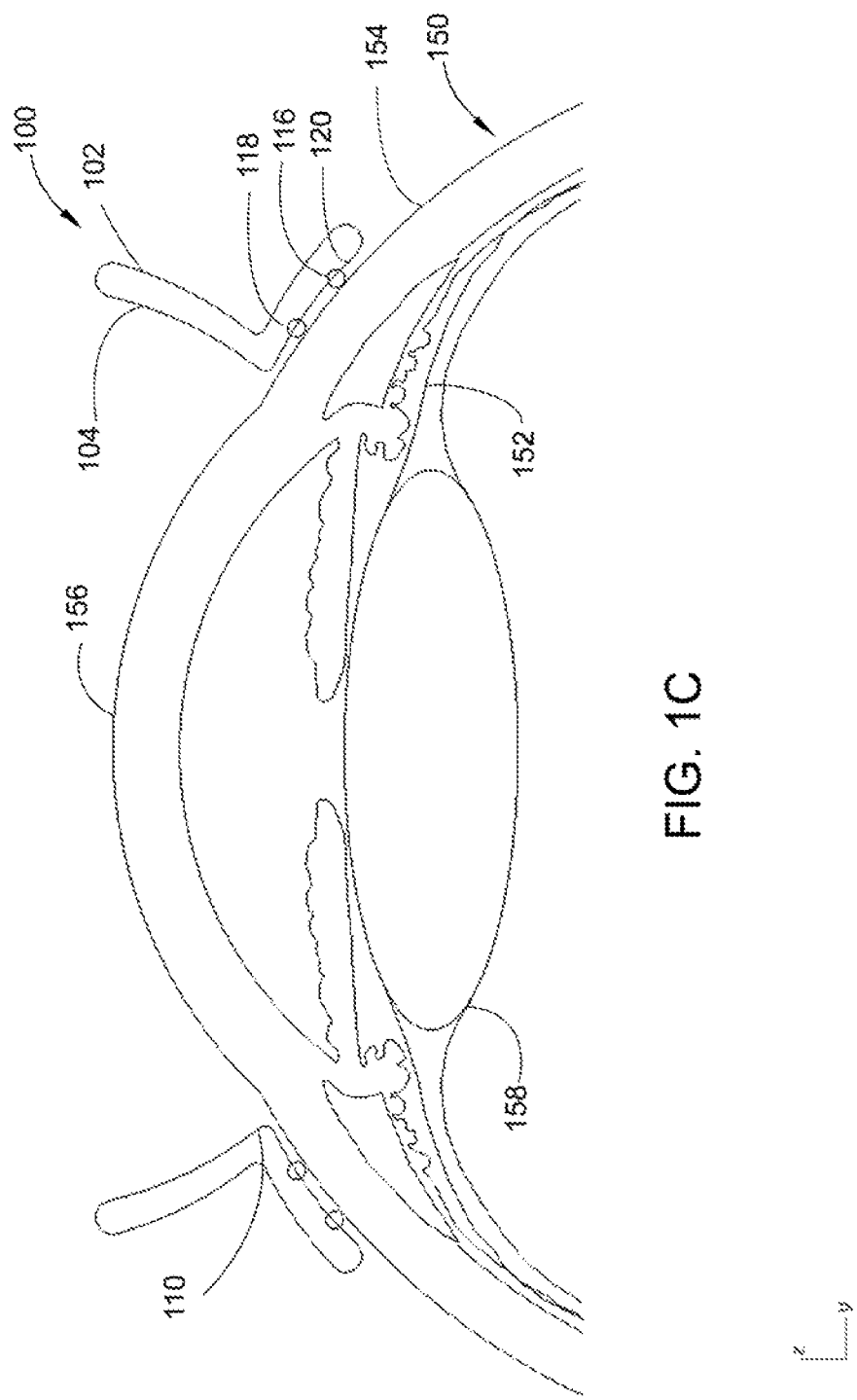
FIG. 1C depicts the accommodation stimulation speculum adapted to contact an eye according to an embodiment.

FIGS. 1A-1C depict an accommodation stimulation device according to an embodiment. In this embodiment, the accommodation stimulation device is an accommodation stimulation speculum 100. Generally, the accommodation stimulation speculum 100 has a speculum body 101, with both an anterior surface 104 and a posterior surface 120, which is adapted to conform to the material features of the eye while expanding to hold the eyelids in either an open or semi-open position. The speculum body 101 can be shaped as two conical frustums which reflect at a convergent plane. The speculum body 101 is formed from a non-conductive material. The posterior surface 120 has one or more electrodes formed thereon. The posterior surface 120 is positioned inward toward the eye 150 while the anterior surface 104 is positioned opposite the posterior surface 120. The anterior surface 104 can have one or more openings to receive connections for the one or more electrodes. Thus, the accommodation stimulation speculum 100 is adapted to deliver electrical stimulation using the pair of electrodes which are positioned in connection with the non-conductive posterior surface 120.

FIG. 1A depicts a frontal view of the accommodation stimulation speculum 100 according to an embodiment. The accommodation stimulation speculum 100 is shown here with a perspective view of the speculum body 101 with an exterior surface 102 and the anterior surface 104. The speculum body 101 can be formed of a material which is safe for use in the eye. The speculum body 101 is both sterilizable (e.g. non-porous) and non-conductive. Examples of possible materials include polymers, such as silicones, plastics and elastomers, or combinations thereof. In further embodiments, the speculum body 101 can comprise two or more materials, such as an inner portion (core) composed of a first material, such as a ceramic, and an outer portion (coating) composed of a plastic with an elastomer.

A first port 112 and a second port 114 are formed in the anterior surface 104. The position of the first port 112 and the second port 114 can be changed according to the needs of the user. The first port 112 can receive a first connection 106 and the second port 114 can receive a second connection 108. The first connection 106 and the second connection 108 can extend out from the anterior surface 104 of the speculum body 101. The speculum body 101 is formed from a non-conductive or insulating material whereas the first connection 106 and the second connection 108 are made from a conductive material, such as a metal (e.g. copper, silver, platinum, palladium, or aluminum), conductive polymers or combinations thereof. In another embodiment, the first connection 106 and the second connection 108 can be formed of a biocompatible conductive material which is used for fabrication of medical electrodes. Biocompatible conductive materials can include silver, silver chloride, platinum, gold, iridium, stainless steel, tungsten and combinations thereof. Biocompatible materials can further include printable inks from a biocompatible material such as silver ink or silver chloride ink. The first connection 106 and the second connection 108 are electrically connected to an electrical stimulation source, such as an electrical stimulator (not shown). Commercially available electrical stimulators which can be used with one embodiment include the Accupulser Signal Generator, SYS-A310 or the Digital Stimulator, DS8000, both available from World Precision Instruments, Inc. located in Sarasota, Fla. The electrical stimulator can be regulated such that the amplitude, the pulse width and the pulse frequency are maintained with specific parameters, described in more detail with reference to FIG. 1C.

An aperture 110 can be formed in the speculum body 101. The aperture 110 is depicted here as a circular opening, however the aperture 110 can be any shape or size which allows access to the eye. The aperture 110 can be a shape which radiates out from a central point, such as a circle or oval. The edge of the aperture 110 can have a surface texture which is non-abrasive to avoid damage to the eye.

FIG. 1B depicts a second view of the accommodation stimulation speculum 100 according to an embodiment. The speculum body 101 is depicted from the perspective of the posterior surface 120. The posterior surface 120 is the inner surface of the conical frustum which contacts the eye. In this embodiment, the speculum body 101 of the accommodation stimulation speculum 100 is depicted with the first port 112 and the second port 114 extending through the speculum body 101 and connecting the anterior surface 104 to the posterior surface 120. The posterior surface 120 can be coated with a material, such as a soft plastic. The posterior surface 120 includes an outer ring electrode 116 and an inner ring electrode 118. The outer ring electrode 116 can be concentric to the inner ring electrode 118.

The outer ring electrode 116 and the inner ring electrode 118 are electrically connected with the first connection 106 and the second connection 108 through the first port 112 and the second port 114. Depicted here, the outer ring electrode 116 is electrically connected to the first connection 106 through the first port 112 and the inner ring electrode 118 is electrically connected to the second connection 108 through the second port 114. The outer ring electrode 116 and the inner ring electrode 118 can each be formed of the same material or a different material as the first connection 106 and the second connection 108, respectively. Though the inner ring electrode 116 and the outer ring electrode 118 are depicted as formed on the posterior surface 120 of the speculum body 101, the rings may be formed in or embedded in the posterior surface 120, based on the needs or desires of the user.

FIG. 1C depicts the accommodation stimulation speculum 100 adapted to contact an eye 150 according to an embodiment. The depiction shows the eye 150 having cornea 156 formed over a lens 158. At the edge of the cornea 156 is sclera 154, which circumscribes the cornea 156. Located under the sclera 154 is ciliary muscle 152. The ciliary muscle 152 is connected to and manipulates the lens 158 by contraction or extension. Located on top of the sclera 154 and circumscribing the cornea 156 is the accommodation stimulation speculum 100. The aperture 110 of the accommodation stimulation speculum 100 forms an inner circumference circumscribing the cornea 156. The anterior surface 104 of the accommodation stimulation speculum 100 further circumscribes the field of vision from the eye 150 while the exterior surface 102 forms a 'V' shape to hold the eyelids open. The posterior surface 120 of the accommodation stimulation speculum 100 can be adapted to contact the sclera 154 through at least the outer ring electrode 116 and the inner ring electrode 118. In one embodiment, the posterior surface 120 of the accommodation stimulation speculum 100 rests against the sclera 154 of the eye 150 with the two concentric electrodes (e.g. the outer ring electrode 116 and the inner ring electrode 118) resting on and in contact with the sclera 154 above the location of the ciliary muscle 152. In one embodiment, the outer ring electrode 116 and the inner ring electrode 118 are concentric circles which are positioned on a portion of the sclera 154 which corresponds to the inner and outer boundaries of the ciliary muscle 152.

As shown, the aperture 110 can be sized to circumscribe the cornea 156 of the eye 150. As such, the aperture 110 can be of numerous sizes which are within the ranges of human and animal eyes. Further embodiments can include either increased or decreased size of the aperture 110, such that the aperture 110 either covers a portion of the cornea or extends beyond the circumference of the cornea.

In operation, power, such as an electrical current, can be delivered from an electrical stimulation source (not shown) at a specific pulse width, pulse frequency and amplitude using the first connection 106 and the second connection 108, described with reference to FIGS. 1A and 1B. This process is referred to herein as electrostimulation. The pulse train frequencies can be in the range of from about 10 Hz to about 1000 Hz, such as about 200 Hz. The pulse widths can be monophasic or biphasic with durations from about 100 µs to about 1 ms, such as about 600 µs.

Without intending to be bound by theory, it is believed that the use of two concentric ring electrodes provides a more efficient electrostimulation of the ciliary muscle than multiple independent contacts. The ciliary muscle connects to and circumscribes the lens. By contracting or relaxing, the ciliary muscle changes the focus of the lens in the eye. By delivering the electrostimulation around the entirety of the ciliary muscle, it is believed that the entire ciliary muscle is activated simultaneously without selective activation or overactivation at any one point, avoiding strain and providing a better model the native physiology in the eye.

The electrical stimulation is delivered through the first connection 106 and through the outer ring electrode 116 to the sclera 154 and subsequently though the ciliary muscle 152. The power is received by the inner ring electrode 118 and thus by the second connection 108 to complete the circuit. When the electrical current is delivered with the appropriate stimulus characteristics, the ciliary muscle 152 is stimulated to contract thus producing an accommodative response. The ciliary muscle 152 contracts based on the characteristics of the power received and accommodates the lens 158 accordingly. The power flow described above can start at either the first connection 106 or the second connection 108.

In the above described embodiment, the accommodation stimulation speculum 100 is positioned under the eyelid with the outer ring electrode 116 and inner ring electrode 118 positioned over the ciliary muscle 152 and in contact with the respective portion of the sclera 154. The outer ring electrode 116 and inner ring electrode 118 can deliver an external stimulus (e.g. electric current) to the ciliary muscle 152 through the sclera 154. By providing an external stimulus to the ciliary muscle 152 through the sclera 154, accommodation of the lens 158 can be achieved in a quick, painless, non-surgical and non-pharmacological fashion. Further, any results can be reproduced with limited expense and complexity, allowing further study of the eye.

Accommodation Stimulation Scleral Contact Lens and Scleral Annulus

In another embodiment, the accommodation stimulation device can be an accommodation stimulation scleral contact lens. The accommodation stimulation scleral contact lens can both provide electrostimulation for accommodation, such as for presbyopia patients, and provide for comfortable use by a conscious person, both allowing proper spacing between the eye and eyelid and allowing blinking.

Figure 2:
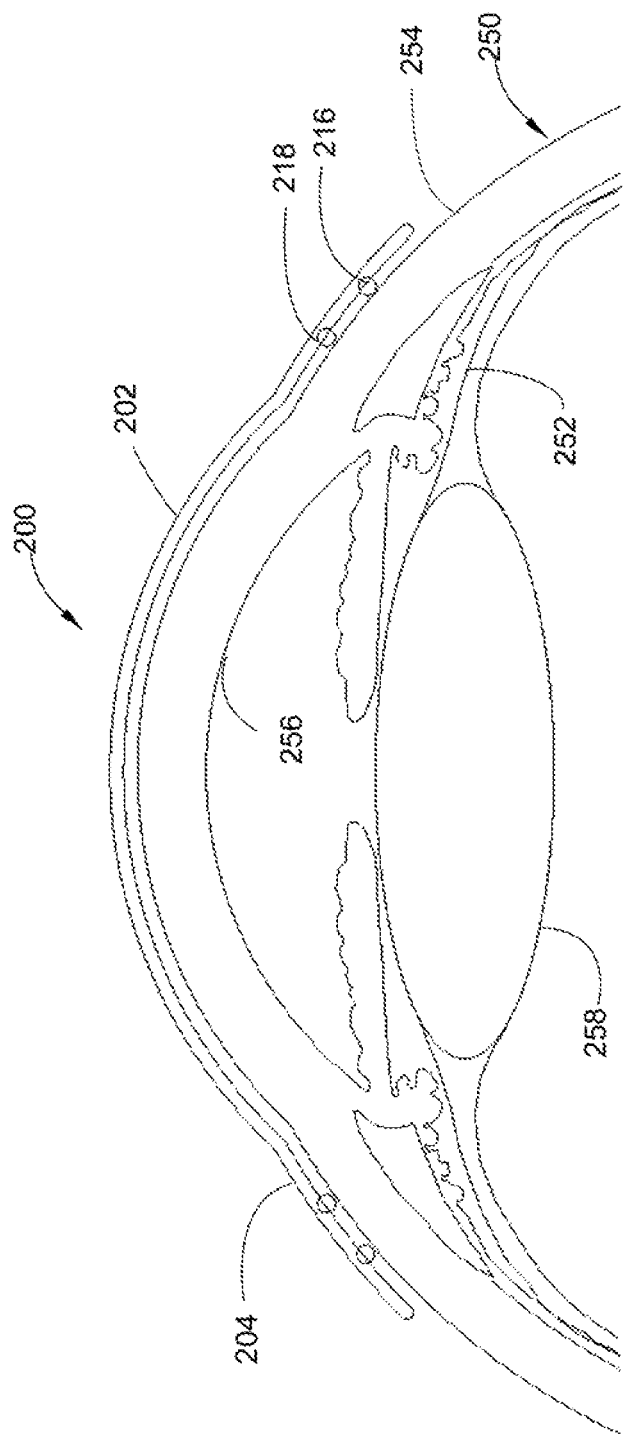
FIG. 2 depicts an accommodation stimulation scleral contact lens adapted to contact an eye according to an embodiment.

FIG. 2 depicts an accommodation stimulation scleral contact lens 200 adapted to contact an eye 250 according to an embodiment. Generally, the accommodation stimulation scleral contact lens 200 includes an external lens region 202 and a scleral contact region 204 and is adapted to conform to the material features of the eye while allowing the eye to function normally. The external lens region 202 is a transparent structure positioned over the cornea 256. The external lens region 202 can be either a corrective or a non-corrective lens. Surrounding the external lens region 202 is the scleral contact region 204. At least the scleral contact region 204 is formed from a non-conductive material. The scleral contact region 204 rests on the sclera 254 and includes one or more electrodes which are positioned or formed on the scleral contact side of the scleral contact region 204. Thus, the accommodation stimulation scleral contact lens 200 is adapted to deliver electrical stimulation using the pair of electrodes which are positioned in connection with the non-conductive scleral contact region 204.

The accommodation stimulation scleral contact lens 200 can include the external lens region 202 which is a convex, transparent structure and the scleral contact region 204. The external lens region 202 can be formed of a variety of materials including polymers, such as hydrophilic plastics. The external lens region 202 can be less than 12 mm in diameter, such as between approximately 7 mm and 10 mm in diameter. Further, the external lens region 202 can be of a standard thickness for contact lenses, such as less than 1 mm thick.

Generally, the external lens region 202 and the scleral contact region 204 are formed as a single structure, without a defined boundary between the external lens region 202 and the scleral contact region 204. The scleral contact region 204 should be non-conductive while the external lens region 202 can be either conductive or non-conductive. In some embodiments, the scleral contact region 204 is coated with a non-conductive material. The scleral contact region 204 is about 5 mm to about 10 mm wide in all directions and circumscribes the external lens region 202. The accommodation stimulation scleral contact lens 200, including both the external lens region 202 and the scleral contact region 204, can have a diameter of from approximately 17 mm to approximately 22 mm. In further embodiments, the scleral contact region 204 and the external lens region 202 are separate components which are connected to form at least a portion of the accommodation stimulation scleral contact lens 200. The scleral contact region 204 and the external lens region 202 can be formed separately and connected to one another, such as through an adhesive. In embodiments where the scleral contact region 204 is a separate component, the scleral contact region 204 can also be formed of a similar material to the speculum body 100, described with reference to FIG. 1A.

An outer ring electrode 216 and an inner ring electrode 218 can be formed in, on or in connection with the scleral contact region 204. The outer ring electrode 216 and the inner ring electrode 218 can have the same attributes and characteristics as described with reference to the outer ring electrode 116 and the inner ring electrode 118 described with reference to FIG. 1A-1C.

The eye 250 is depicted with a cornea 256, a lens 258, a sclera 254 and a ciliary muscle 252, as described above. The ciliary muscle 252 is connected to and manipulates the lens 258 by contraction or extension. Located over the sclera 254 and the cornea 256 is the accommodation stimulation scleral contact lens 200. In one embodiment, the accommodation stimulation scleral contact lens 200 is adapted to contact the eye 250.

The external lens region 202 can be adapted to contact the cornea 256. The external lens region 202 can be a transparent non-correcting lens or it can be a corrective lens, such as a corrective lens for astigmatism, near-sightedness or far-sightedness. The scleral contact region 204 of the accommodation stimulation scleral contact lens 200 can be adapted to contact the sclera 254 through at least the outer ring electrode 216 and the inner ring electrode 218. In one or more embodiments, the scleral contact region 204 is on the sclera 254. In one embodiment, the posterior surface 220 of the accommodation stimulation scleral contact lens 200 rests against the sclera 254 of the eye 250 with the two concentric electrodes (e.g. the outer ring electrode 216 and the inner ring electrode 218) resting on the sclera 254 above the location of the ciliary muscle 252.

As described with reference to FIG. 1C, external stimulation at specific frequencies, pulse widths and amplitudes can be delivered such that contraction of the ciliary muscle 252 and subsequent accommodation of the lens 258 can be achieved. In this embodiment, the electrostimulation of the ciliary muscle 252 can create accommodation of the lens 258 in combination with correction by using the external lens region 202.

One or more electrical connections (not shown) can be formed in or through the scleral contact region 204. The electrical connections form an electrical pathway between the concentric electrodes using the electrical stimulation source (not shown). The electrical stimulation source can be either internal or external to the lens. The electrical stimulation source can a battery, a kinetic power source, a solar power source or others. In one embodiment, electrical connections extend through the scleral contact region 204 and are connected to an electrical stimulation source which is carried on the head of the user. The electrostimulation in this embodiment can be activated based on physiological detectors, such as by physiological changes associated with an attempt at accommodation by the patient, or it can be activated manually, such that the patient can self-manipulate the accommodation response at the lens 258.

Though described with reference to a single accommodation stimulation device (e.g. the accommodation stimulation speculum 100 and accommodation stimulation scleral contact lens 200), it is understood that an accommodation stimulation device can be used on each eye. In further embodiments, the accommodation stimulation devices can be used on each eye where each accommodation stimulation device is connected in parallel to a single electrical stimulation source to achieve binocular (both eyes) accommodation, described hereafter as "daisy chaining" of the devices. Daisy chaining can allow the connected accommodation stimulation devices to work in synch with each other, which can facilitate studying the accommodative response in both eyes together.

Without intending to be bound by theory, local stimulation of the embodiments described above is not believed to interfere with motor control of the eye by the patient or user. The electrical stimulation device stimulates the ciliary muscle with electrodes positioned proximate to the ciliary muscle. By properly positioning the electrodes, the electrical impulse does not travel beyond the ciliary muscle and the sclera, thus stimulating only the ciliary muscle. Since the electrical stimulation devices only stimulate the ciliary muscle in a localized way and don't stimulate the extraocular muscles, the accommodation stimulation would not produce convergence eye movements. Convergence eye movement is the phenomenon where the two eyes normally move towards each other when attempting to focus on a near object. This uncoupling of accommodation and convergence provides for an increased ability to focus the lens without moving the eye as a consequence of the accommodation stimulation.

The accommodation stimulation scleral contact lens 200 disclosed here can deliver electrostimulation while providing a comfortable and useable means to elicit accommodation in a conscious human and to keep the device on the eye 250. In this embodiment, the inner ring electrode 218 and the outer ring electrode 216 reside only over the sclera 254 of the eye 250 and may therefore be comfortable to wear on the eye 250.

Figure 3:
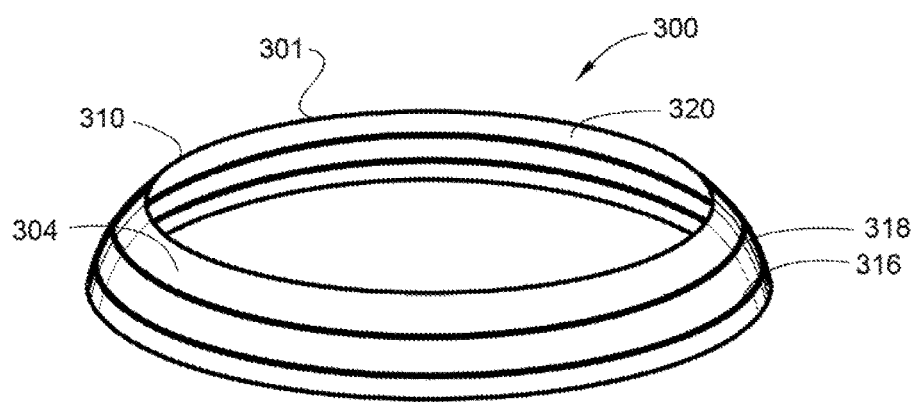
FIG. 3 depicts an accommodation stimulation scleral annulus adapted to contact an eye according to an embodiment.

FIG. 3 depicts an accommodation stimulation scleral annulus 300 according to an embodiment. The accommodation stimulation scleral annulus 300 is depicted with an annulus body 301 which substantially conforms to the shapes and curvatures of the eye (not shown). The annulus body 301 can be composed of a material such as those used in conjunction with the accommodation stimulation speculum 100 or the accommodation stimulation scleral contact lens 200, described with reference to FIGS. 1 and 2 respectively.

An opening 310 is formed in the annulus body 320 which circumscribes the cornea of the eye. The annulus body 301 has an anterior surface 304 and a posterior surface 320. The posterior surface 320 rests above or on the sclera of the eye such that an outer ring electrode 316 and an inner ring electrode 318 are brought in electrical contact with the sclera. As above, the outer ring electrode 316 and the inner ring electrode 318 are positioned over a region of the sclera which corresponds to the area of the underlying ciliary muscle. The annulus body 310 can be of an approximately equal width, as depicted, and can be sized to appropriately correspond to the eye of the user.

In operation, accommodation of the lens 258 is achieved in the absence of an external lens, such as the external lens region 202 described with reference to FIGS. 2A and 2B. The external stimulation at specific frequencies and amplitudes is delivered through the outer ring electrode 316 and the inner ring electrode 318 to create contraction of the ciliary muscle and subsequent accommodation of the lens in the eye.

Accommodation Devices with Vacuum Suction

In another embodiment, the accommodation stimulation device can be a vacuum suction accommodation stimulation speculum or a vacuum suction accommodation stimulation scleral contact lens. In the vacuum suction accommodation stimulation speculum or scleral contact lens, vacuum suction is employed to stabilize the speculum or the scleral contact lens on the eye and to improve the contact of the inner and outer ring electrodes against the sclera. The embodiments below are described with reference to the speculum design but it is understood that the vacuum suction described here can be incorporated into other disclosed designs, such as the accommodation stimulation scleral contact lens or the accommodation stimulation scleral annulus.

Figure 4A:
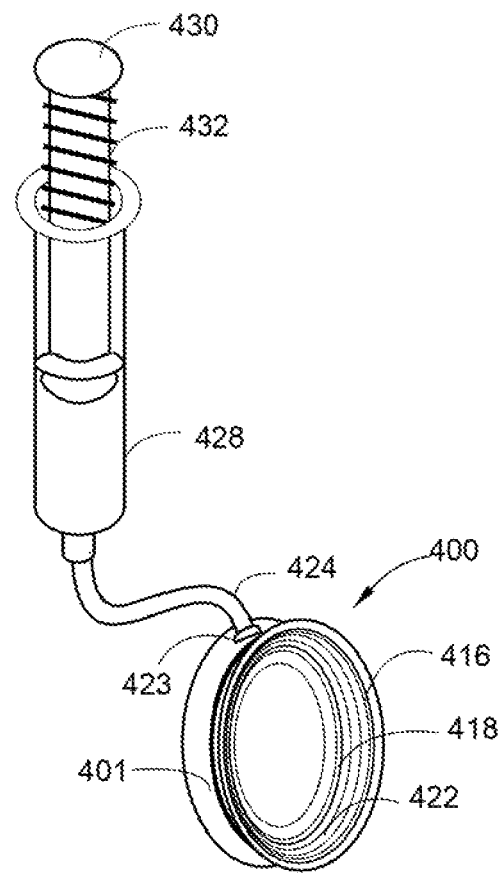
FIG. 4A depicts a rear view of a vacuum suction accommodation stimulation device according to an embodiment.
Figure 4B:
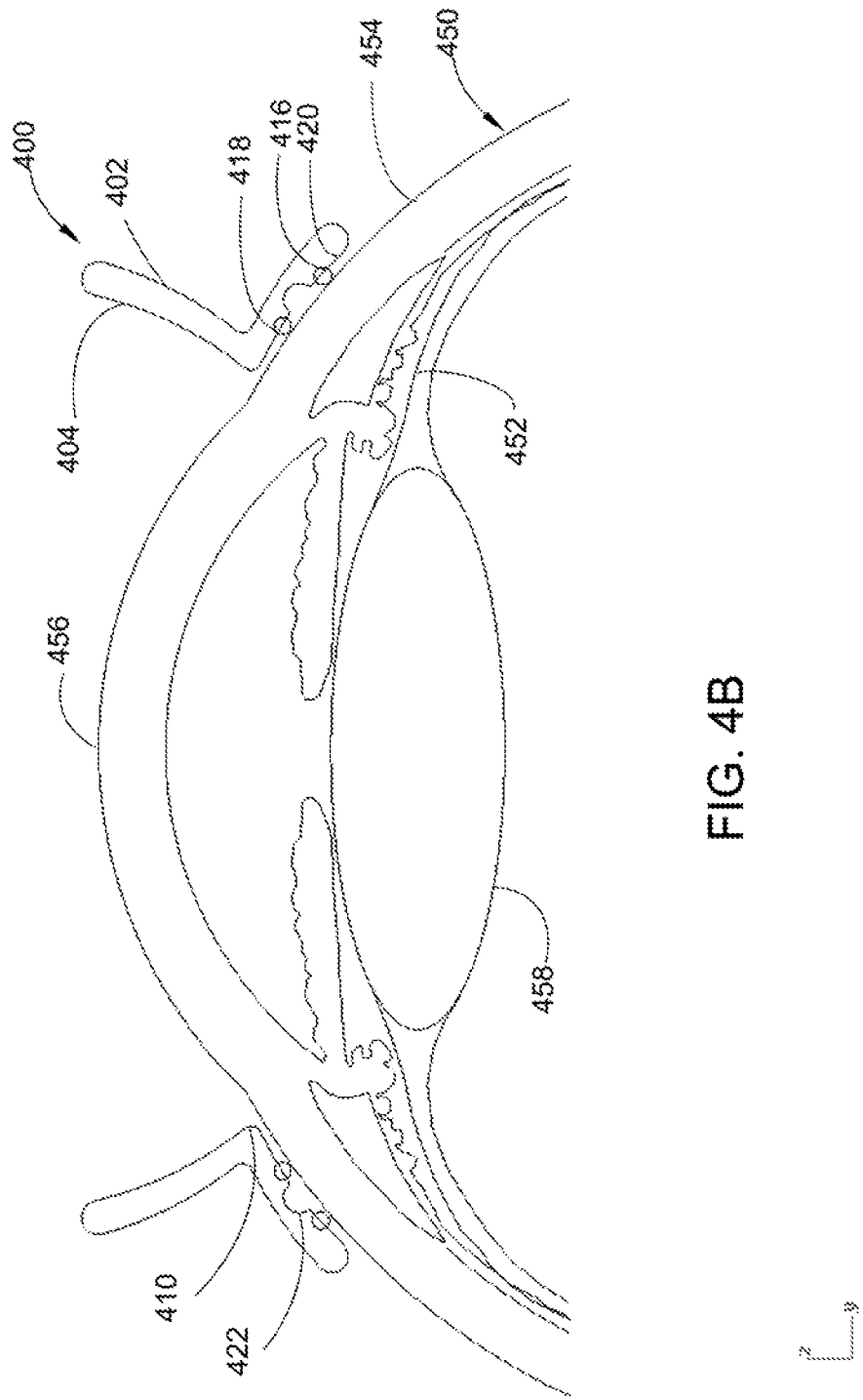
FIG. 4B depicts the vacuum suction accommodation stimulation device adapted to contact an eye according to an embodiment.

FIGS. 4A and 4B disclose a vacuum suction accommodation stimulation speculum 400 according to an embodiment. FIG. 4A depicts a rear view of the vacuum suction accommodation stimulation speculum 400 according to an embodiment. The vacuum suction accommodation stimulation speculum 400 can have a speculum body 401, an anterior surface (not visible here), a posterior surface 420, and other components as described with reference to FIGS. 1A-1C. It is understood, that shapes, sizes, compositions and other physical characteristics described with reference to the accommodation stimulation speculum 100 can be incorporated into the vacuum suction accommodation stimulation speculum 400 without further recitation.

The speculum body 401 is depicted with the posterior surface 420. The posterior surface 420 can have an outer ring electrode 416 and an inner ring electrode 418. The outer ring electrode 416 and the inner ring electrode 418 can be substantially similar to the outer ring electrode 116 and the inner ring electrode 118 described with reference to FIGS. 1A-1C. Further, the posterior surface 420 can have a vacuum opening 422 formed therein. The vacuum opening 422 can be any form of opening such as holes/pores, linear grooves, specific shapes or combinations thereof. In this embodiment, the vacuum opening 422 is depicted as a groove. The vacuum opening 422 can be positioned anywhere on the posterior surface 420 such that secure contact between the outer ring electrode 416 and the inner ring electrode 418 can be established. In one embodiment, the vacuum opening 422 is a channel or groove positioned between the outer ring electrode 416 and the inner ring electrode 418. Though the vacuum opening 422 is depicted here as a single opening, the vacuum opening 422 can be a plurality of separate openings of various shapes and sizes.

The vacuum opening 422 can be in fluid connection with a vacuum line 424 through a vacuum contact 423. The vacuum contact 423 can connect through the speculum body 401 to the vacuum opening 422 such that the vacuum can be created by an exterior source and delivered to the vacuum opening 422 in a controlled fashion. The vacuum contact 423 can direct vacuum from the exterior source such that the vacuum delivered through the vacuum opening 422 is uniform. The vacuum is then delivered through the speculum body 401 to the vacuum opening 422.

The vacuum in the vacuum opening 422 can be achieved using vacuum-creating devices or methods, such as by using a spring-loaded syringe, a vacuum pump or other suction source connected with a vacuum opening 422 on the speculum body 401. In this embodiment, vacuum is achieved by placing a spring 432 around or in the plunger 430 connected with a syringe base 428. The vacuum line 424 is shown as attached from the syringe base 428 to the vacuum contact 423 of the speculum body 401.

FIG. 4B depicts the vacuum suction accommodation stimulation speculum 400 adapted to contact an eye 450 according to an embodiment. The depiction here shows the eye 450 has a cornea 456 formed over a lens 458. At the edge of the cornea 456 is the sclera 454, which circumscribes the cornea 456. Located under the sclera 454 is the ciliary muscle 452. The ciliary muscle 452 is connected to and manipulates the lens 458 by contraction or extension. Located on top of the sclera 454 and circumscribing the cornea 456 is the accommodation stimulation speculum 400. The posterior surface 420 of the accommodation stimulation speculum 400 can be adapted to contact the sclera 454 through at least the outer ring electrode 416 and the inner ring electrode 418. The vacuum opening 422 is depicted as formed between the outer ring electrode 416 and the inner ring electrode 416. The vacuum opening 422 in this embodiment is a channel formed between and alongside the inner ring electrode 418 and the outer ring electrode 416 which is approximately central to the ciliary muscle 452. In one embodiment, the posterior surface 420 of the accommodation stimulation speculum 400 rests against the sclera 454 of the eye 450 with the two concentric electrodes (e.g. the outer ring electrode 416 and the inner ring electrode 418) resting on the sclera 454 above the location of the ciliary muscle 452.

In operation, plunger 430 is depressed into the syringe base 428, shown with reference to FIG. 4A. The spring 432 applies force to the syringe base 428 in an opposite direction from the force the spring 432 applies to the plunger 430. Thus, the plunger 432 creates suction in the syringe body 428 which is proportional to the force applied by the spring 432. The suction in the syringe body 428 is translated through the vacuum line 424 to the vacuum opening 422 in the speculum body 401. As described above, the speculum body 401 has a channel or a groove formed in the posterior surface 420 so that the suction creates a vacuum between the posterior surface 420 and the sclera 454, thus pulling and holding the speculum body 401 onto the eye 450. As described with reference to FIG. 1C, external stimulation of specific frequencies and amplitudes can be delivered such that contraction of the ciliary muscle 452 and subsequent accommodation of the lens 458 can be achieved.

In the above embodiment, a vacuum suction accommodation stimulation speculum 400 is disclosed. By forming a vacuum between the sclera 454 and the posterior surface 420, the vacuum suction accommodation stimulation speculum 400 can be held in better position and the inner and outer ring electrodes 416, 418 can be brought into more intimate contact with the sclera 454. By forming a vacuum between the two surfaces, mobility of the vacuum suction accommodation stimulation speculum 400 can be decreased and better delivery of electrostimulation to the ciliary muscle 452 can be achieved.

Scleral Stimulation of Accommodative Intraocular Lens

FIG. 5 depicts a accommodation stimulation contact lens 500 adapted to contact an eye 550 according to an embodiment. The accommodation stimulation contact lens 500 can comprise a external lens 502 and a scleral contact region 504 as described with reference to FIG. 2. An outer ring electrode 516 and an inner ring electrode 518 can be formed in, on or in connection with the scleral contact region 504. The outer ring electrode 516 and the inner ring electrode 518 can have the same attributes and characteristics as described with reference to the outer ring electrode 116 and the inner ring electrode 118 described with reference to FIG. 1A-1C.

The accommodation stimulation contact lens 500 is depicted in contact with the eye 550. The eye 550 is depicted with a cornea 556, a sclera 554 and a ciliary muscle 552, as described above with reference to FIG. 1C. The ciliary muscle 552 is connected to and manipulates the accommodative intraocular lens 558 by contraction or extension. Located on top of the sclera 554 and the cornea 556 is the accommodation stimulation contact lens 500.

The external lens 502 can be adapted to contact the cornea 556. The external lens 502 can be simply transparent or it can be corrective, such as for astigmatism, near-sightedness or far-sightedness. The scleral contact region 504 of the accommodation stimulation scleral contact lens 500 can be adapted to contact the sclera 554 through at least the outer ring electrode 516 and the inner ring electrode 518. In one or more embodiments, the scleral contact region 504 is directly on the sclera 554. In one embodiment, the posterior surface 520 of the accommodation stimulation contact lens 500 rests against the sclera 554 of the eye 550 with the two concentric electrodes (e.g. the outer ring electrode 516 and the inner ring electrode 518) resting on the sclera 554 above the location of the ciliary muscle 552.

In this embodiment, the natural lens of the eye 550 has been replaced by the accommodative intraocular lens 558. The accommodative intraocular lens 558 comprises a transparent electroactive polymer. The accommodative intraocular lens 558 can incorporate other materials, such as polymers described with reference to the external lens 502, 302, so long as the accommodative intraocular lens 558 remains responsive to the externally applied electrostimulation.

As described with reference to FIG. 1C, electrostimulation at specific frequencies, pulse widths and amplitudes can be delivered such that contraction of the ciliary muscle 552 and subsequent accommodation of the accommodative intraocular lens 558 can be achieved. In this embodiment, dual accommodation can be achieved by using the external lens 502 in conjunction with the electrostimulation of the ciliary muscle 552. The electrical connections and power source used in this embodiment can be the same as those described with reference to FIG. 3. When an electrical stimulus is received by the ciliary muscle during electrostimulation from the power source, the electrical stimulus is also received by the accommodative intraocular lens 558. The ciliary muscle 552 contracts and the accommodative intraocular lens 558 moves in a corresponding fashion to produce accommodation. As described above, the electrostimulation in this embodiment can be activated based on physiological detectors or it can be activated manually, such that the patient can self-manipulate the dual accommodation response of the accommodative intraocular lens 558.

Though this embodiment is described with reference to the accommodation stimulation scleral contact lens 500, other embodiments described herein are expected to provide the same dual accommodation benefit. In one embodiment, the accommodation stimulation speculum 100 can be used in place of the accommodation stimulation scleral contact lens 500 to achieve accommodation at the accommodative intraocular lens 558.

In the above described embodiment, the electrostimulation delivered through the accommodation stimulation scleral contact lens 500 is received by both the ciliary muscle 552 and the accommodative intraocular lens 558 to create the accommodative response. This technology can provide numerous benefits, especially for patients that, due to a disease state, have lost use of the natural lens. For example, cataracts cloud the natural lens and presbyopia causes a loss of natural accommodation. By the described methods and apparatus, natural accommodation and sight or better can be restored.

The accommodative intraocular lens as described herein can be used to restore accommodation to the presbyopic eye. Accommodative intraocular lenses may be implanted in the eye during a non-related procedure, such as cataract surgery. The implanted accommodative intraocular lens can then undergo accommodation in response to ciliary muscle contraction. In further embodiments, other restorative events which increase the flexibility may be used in combination with the accommodation devices described above. One restorative event can be a medication that is intended to be administered to the eye and diffuse into the presbyopic lens, where the medication softens the lens to restore accommodation. Another restorative event can be a laser surgical procedure in which one or more laser cuts are made in the presbyopic lens, such that the overall stiffness of the lens is reduced, to restore the accommodative ability to the presbyopic lens.

In any of these procedures or any other accommodation restoration procedures, it may be advantageous to stimulate the ciliary muscle during the treatment or following the treatment. Electrically stimulated accommodation could be used for facilitating the efficacy of the treatment, such as to facilitate the diffusion of the drug into the lens by using electrically stimulated ciliary muscle contraction to effectively massage the lens. Electrically stimulated accommodation could be used after laser cuts are made into the lens to facilitate the effectiveness of the laser cuts in softening the lens. In another embodiment, electrically stimulated accommodation could be used intraoperatively after a surgeon has introduced an accommodative intraocular lens into the eye to ensure optimal positioning of the intraocular lens in the eye or to allow the surgeon to observe if the intraocular lens is undergoing accommodative changes in response to electrically stimulated ciliary muscle contraction.

The accommodation stimulation devices described herein can also be used for measuring the electrical activity produced at or received by the ciliary muscle. The ciliary muscle generates electrical impulses when it contracts as part of a voluntary effort to accommodate. The electrodes of the accommodation stimulation devices described above are generally positioned immediately above the ciliary muscle. As such, it is believed that the electrodes may be ideally suited to record the ciliary muscle electrical activity.

Ciliary muscle activity can be recorded when a patient or user makes a voluntary accommodative effort, such as when the patient or user attempts to focus on a near object. Recording ciliary muscle activity is believed to be useful in a variety of activity measurement situations, such as for measuring the magnitude of the ciliary muscle contraction, for measuring the magnitude of an accommodative effort a patient or user produces, for determining if the ciliary muscle is contracting when a patient or user makes an effort to focus or for using the recorded ciliary muscle electrical activity as a trigger effect to trigger stimulation from the accommodation stimulation device. In one embodiment, the ciliary muscle produces an electrical signal in response to an attempt by the patient or user to accommodate. This electrical signal is received by the accommodation stimulation device and measured at either the accommodation stimulation device or a detection device. The received electrical signal can be recorded without further interaction or it can be used as an indicia for a secondary event. Secondary events can include, but are not limited to, the received signal being used to trigger the delivery of external stimulation from the accommodation stimulation device. The external stimulation can be at a frequency and amplitude as described above with reference to FIG. 1C.

Further applications of electrical stimulation of accommodation, using one or more of the embodiments described above, include situations when accommodation cannot be stimulated by other means. There may be circumstances where it is not possible to get a patient to elicit a visual stimulus driven or a voluntary elicited accommodative response. Such situations include in a blind eye where the eye cannot perceive a near target or cannot perceive a blurred image. Further examples include an eye with a large depth of focus due to optical aberrations such as astigmatism or spherical aberration, or in eyes that may have degraded vision such as from clouding of the lens such as cataract. In cases such as this, standard methods for eliciting accommodation in an eye by presenting the eye with a visual stimulus may not be effective. In these instances, electrically stimulated accommodation using the embodiments described herein may provide a mechanism of determining the accommodative amplitude or the accommodative potential of the eye.

Further applications of electrically stimulated accommodation include in experiments on animals. Animals are often used to study accommodation and presbyopia or to do research on accommodation and presbyopia or to study accommodation restoration concepts or to study procedures aimed at reversing presbyopia. Electrical stimulation of accommodation in animal models can require invasive surgical procedures to expose nerves that enter the eye or to insert electrodes into the brain centers that control accommodation. The use of an electrode that is placed on the animal eye to stimulate accommodation, substantially decreases risk of injury to the animal while providing substantially similar results in a non-invasive fashion. This approach also allows accommodation to be stimulated in any animal without any other prior preparatory procedures having been performed on the animal.

EXAMPLES

FIGS. 6A-6C are graphical depictions of measurements related to accommodative responses created by an accommodation stimulation device according to the embodiment described with reference to FIGS. 1A-1C. FIG. 6A shows a graph 600 depicting five individual, dynamically recorded, accommodative responses. The responses were recorded using an infra-red light-based photorefractor. Infra-red light based photorefractors which can be modified for embodiments of this invention include the Accommodation Meter from PlusOptix, Inc., located in Nuremberg, Germany. The y-axis depicts the accommodation measured in Diopters (D) and the x-axis is time measured in seconds (s) from an arbitrary start point prior to the beginning of accommodative stimulation.

Each of the five measurements depict a rapid onset of accommodation with a plateau of approximately 8 Diopters. The accommodative response was stimulated for approximately 4 seconds, with the response plateau being maintained for approximately 2.5 seconds. Graph 600 further shows the accommodative response with low noise, reflecting a controlled accommodation which is not limited by variability in basal ciliary muscle tone. Once the electrical stimulation from the accommodation stimulation device was stopped, the eye rapidly returned to the baseline state. Thus, accommodation is achievable in a rapidly inducible fashion with limited noise using the accommodation stimulation devices described above.

FIG. 6B shows a graph 620 depicting the durations of the electrical pulse-trains, as delivered to the ciliary muscle to achieve the accommodative response. The electrical impulses depicted were recorded at an intermediate stimulus amplitude of 30% of the maximum possible, as described with reference to FIG. 1C. Graph 620 shows a rapid transition between the delivery of the electrical impulses and cessation of the electrical impulses. Each of the five electrical pulse-trains lasted for approximately four seconds with a sharp rise to the desired level of electrical input and a sharp fall to baseline.

Thus, FIGS. 6A and 6B together show that accommodation is achieved controllably, reversibly and with direct correlation to the electrical stimulation delivered by the accommodation stimulation device. Each stimulation closely correlates with the measured optical change, or accommodative response, of the eye. Further, the electrical stimulations are capable of maintaining the level of accommodation desired for the period of time desired, as correlated to the plateau of the impulse.

FIG. 6C shows a graph 640 depicting the velocity of accommodation according to an embodiment. The velocities shown in FIG. 6C are the velocities achieved in the accommodative responses shown in FIG. 6A using the electrical stimulation depicted in FIG. 6B. The velocity profiles are calculated using a two point difference calculation.

Observable in graph 640, the velocity of both the accommodation and the relaxation of accommodation is sharp and definable, when using the above described accommodation stimulation device. Noise is a common difficulty in accommodative measurement. Accommodation eliciting techniques, such as visual stimulus elicited accommodation, are generally limited by the strength and tone of the ciliary muscle. Thus, accommodation stimulated using these accommodation stimulation techniques tend to create variability in the accommodative response resulting in background noise unrelated to the accommodation event. This background noise is compounded during subsequent data processing, such as determination of velocity, which can make this derivative data either less precise or unusable. The low noise accommodation data, described with reference to FIG. 6A, is therefore particularly amenable to various kinds of analysis (such as the velocity profile calculations) that would not normally be possible with data which includes more noise, such as accommodation data collected and studied from voluntary accommodation or with visual stimulus elicited accommodation.

FIGS. 7A-7C depict a plurality of stimulated accommodative responses using the accommodation stimulation device described above with reference to FIGS. 6A-6C. FIG. 7A is a graph 700 of elicited and measured accommodative responses over an extended period of time. The accommodative responses were produced by electrical stimulation, shown with reference to graph 720 of FIG. 7B. Measurements were performed using the accommodation stimulation device described with reference to FIGS. 1A-1C and using parameters described with reference to FIGS. 6A-6C. Graph 700 shows 20 individual accommodative responses with an average maximum amplitude of approximately 7 Diopters which were elicited by the accommodation stimulation device. The accommodative responses were elicited and recorded over a period of 170 seconds.

FIG. 7B shows a graph 720 depicting the durations of the electrical pulse-trains, as delivered to the ciliary muscle to achieve the accommodative response. The electrical impulses depicted were delivered at an intermediate stimulus amplitude of 30% of the maximum possible and at a constant frequency and pulse-width, as described with reference to FIG. 1C.

FIG. 7C is a graph 740 depicting the velocities of the accommodative responses stimulated by the accommodation stimulation device. Velocities shown here were calculated from the accommodative responses described with reference to FIG. 7A.

Graph 740 depicts the time of onset and termination of each of the 20 responses and the calculated velocity profile of each of the 20 individual accommodative responses. The calculated velocity includes the velocity of both the accommodation event (positive numbers) and the relaxation of accommodation (negative numbers). The velocity of accommodation and the velocity of relaxation of accommodation is consistent and is maintained over the 20 stimulations, as delivered over a time period of 140 seconds.

Figure 8D:
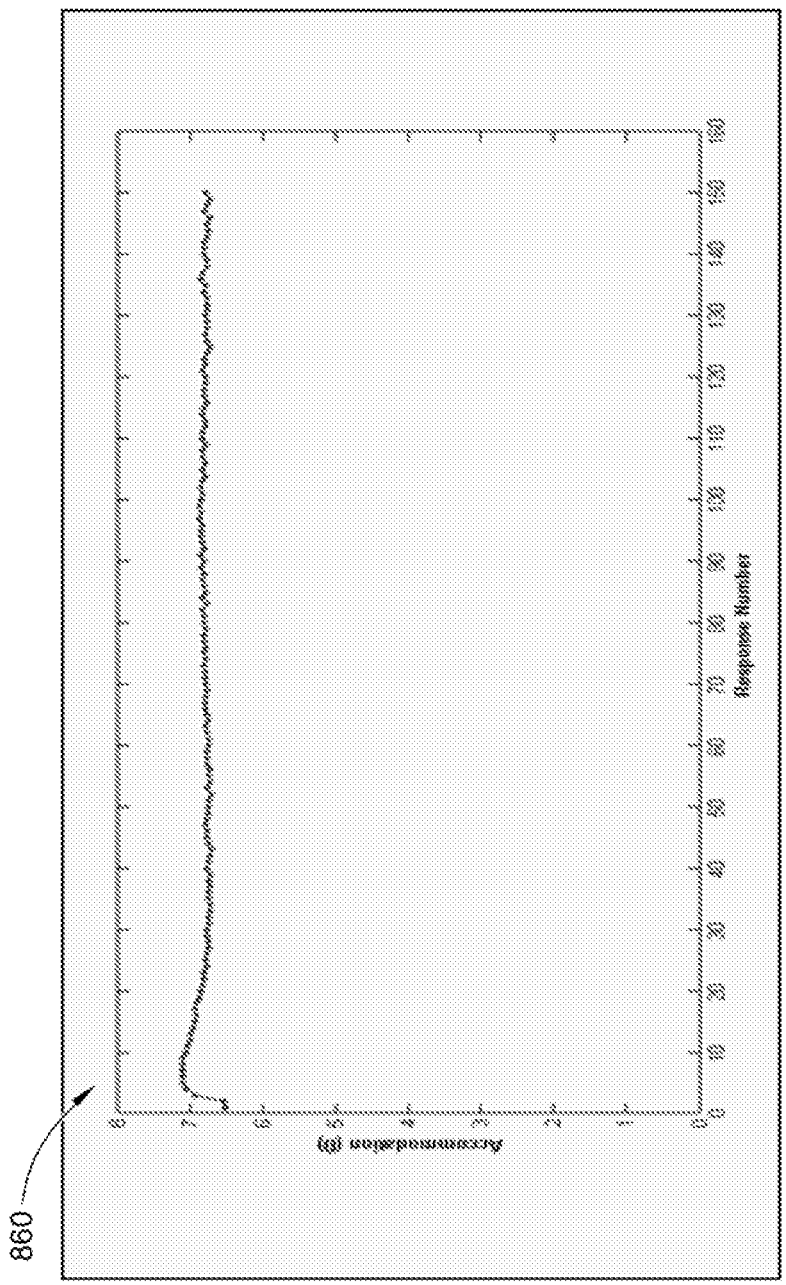

FIGS. 8A-8D depict a plurality of stimulated accommodative responses using the device described above with reference to FIGS. 6A-6C. FIG. 8A is a graph 800 of elicited and measured accommodative responses over an extended period of time. The accommodative responses were produced by electrical stimulation, shown with reference to graph 820 of FIG. 8B. Accommodation was stimulated using the accommodation stimulation device described with reference to FIGS. 1A-1C and using parameters described with reference to FIGS. 6A-6C. Graph 800 shows 150 individual accommodative responses with a maximum amplitude of approximately 7 Diopters which were elicited by the accommodation stimulation device. The accommodative responses were elicited and recorded continuously over a period of 20 minutes.

FIG. 8B shows a graph 820 depicting the durations of the electrical pulse-trains, as delivered to the ciliary muscle to achieve the accommodative response. The electrical impulses depicted were recorded at an intermediate stimulus amplitude of 30% of the maximum possible and a constant frequency of 200 Hz, as described with reference to FIG. 1C.

FIG. 8C is a graph 840 depicting the velocities of the accommodative responses stimulated by the accommodation stimulation device. Velocities shown here were calculated from the accommodative responses described with reference to FIG. 8A as achieved using the accommodation stimulation device described with reference to FIGS. 1A-1C. The stimulation and relaxation velocities of the accommodative responses can be consistently measured over an extended period of time.

It is believed that, since this is an intermediate amplitude response, increasing the stimulus amplitude will result in a further increase in the response amplitude, up to the maximum accommodative response in an individual. Thus, a stimulus amplitude sufficient to achieve the full accommodative response can be used and the accommodative responses would similarly be sustained for protracted periods and durations of accommodation stimulation.

FIG. 8D depicts a graph 860 of the maximum accommodative response amplitudes of each accommodative response. As stated above, the maximum accommodative response amplitude observed was approximately 7 Diopters as measured in 150 stimulated accommodative responses. Shown here, there is no significant change in magnitude of accommodative response amplitudes during many repeated accommodation stimulations, even over an extended period of time. As stated above, since these are intermediate accommodative response amplitudes, using a higher stimulus amplitude would result in a higher accommodative response amplitude.

FIGS. 9A-9C depict a plurality of stimulated accommodative responses using the accommodation stimulation device described above with reference to parameters used in FIGS. 6A-6C. FIG. 9A is a graph 900 depicting elicited and measured accommodative responses over an extended period of time. The accommodative responses were produced by electrical stimulation, shown with reference to graph 920 of FIG. 9B. Measurements were performed using the accommodation stimulation device described with reference to FIGS. 1A-1C and using parameters described with reference to FIGS. 6A-6C. Graph 900 shows 5 individual accommodative responses with a maximum amplitude of approximately 8 Diopters which were elicited by the accommodation stimulation device. The accommodative responses were elicited and recorded over a period of 80 seconds.

FIG. 9B shows a graph 920 depicting increased stimulus pulse-train durations compared to the preceding 4-second pulse-train durations in the preceding graphs, as delivered to the ciliary muscle to achieve the accommodative response. The stimulus pulse-train durations were approximately 10 seconds. The electrical pulse-trains depicted were delivered at an intermediate stimulus amplitude of 30% of the maximum possible and a constant frequency of 200 Hz, as described with reference to FIG. 1C.

FIG. 9C is a graph 940 depicting the velocities of the accommodative responses stimulated by the accommodation stimulation device. Velocities shown here were calculated from the accommodative responses described with reference to FIG. 9A.

FIGS. 10A-10C depict a plurality of stimulated accommodative responses using the device described above with reference to parameters used in FIGS. 6A-6C. FIG. 10A is a graph 1000 of elicited and measured accommodative responses over an extended period of time. The accommodative responses were produced by electrical stimulation, shown with reference to graph 1020 of FIG. 10B. Measurements were performed using the accommodation stimulation device described with reference to FIGS. 1A-1C and using parameters described with reference to FIGS. 6A-6C. Graph 1000 shows 5 individual accommodative responses with a maximum amplitude of approximately 9 Diopters which were elicited by the accommodation stimulation device. The accommodative responses were elicited and recorded over a period of 130 seconds.

FIG. 10B shows a graph 1020 depicting increased stimulus pulse-train durations, as delivered to the ciliary muscle to achieve the accommodative response. The stimulus pulse-train durations were approximately 20 seconds. The electrical impulses depicted were recorded at an intermediate stimulus amplitude of 30% of the maximum possible with a constant frequency of 200 Hz, as described with reference to FIG. 1C.

FIG. 10C is a graph 1040 depicting the velocities of the accommodative responses stimulated by the accommodation stimulation device. Velocities shown here were calculated from the accommodative responses described with reference to FIG. 10A.

FIGS. 11A-11C depict a plurality of stimulated accommodative responses using the device described above with reference to parameters used in FIGS. 6A-6C. FIG. 11A is a graph 1100 of elicited and measured accommodative responses over an extended period of time. The accommodative responses were produced by electrical stimulation, shown with reference to graph 1120 of FIG. 11B. Measurements were performed using the accommodation stimulation device described with reference to FIGS. 1A-1C and using parameters described with reference to FIGS. 6A-6C. Graph 1100 shows 5 individual accommodative responses with a maximum amplitude of approximately 8 Diopters which were elicited by the accommodation stimulation device. The accommodative responses were elicited and recorded over a period of 180 seconds.

FIG. 11B shows a graph 1120 depicting increased stimulus pulse-train durations, as delivered to the ciliary muscle to achieve the accommodative response. The stimulus pulse-train durations were approximately 30 seconds. The electrical impulses depicted were recorded at an intermediate stimulus amplitude of 30% of the maximum possible, as described with reference to FIG. 1C.

FIG. 11C is a graph 1140 depicting the velocities of the accommodative responses stimulated by the accommodation stimulation device. Velocities shown here were calculated from the accommodative responses described with reference to FIG. 11A.

Thus, as depicted in FIGS. 9A-11C, the increased duration of the stimulus pulse-trains show that accommodation can be reliably and repeatedly achieved over multiple intermediate or long duration stimulus pulse-trains, even with complete relaxation between accommodative stimulations. Further, the accommodation velocities and the relaxation of accommodation velocities remain constant between stimulations, showing that the methods, systems and apparatus described here can reliably achieve accommodation without significant change in the velocity of the response or the return to baseline.

FIGS. 12A-12C depict a single extended stimulated accommodative response using the device described above with reference to FIGS. 6A-6C. FIG. 12A is a graph 1200 of elicited and measured accommodative responses over an extended period of time. The accommodative response was produced by electrical stimulation, shown with reference to graph 1220 of FIG. 12B. Measurements were performed using the accommodation stimulation device described with reference to FIGS. 1A-1C and using parameters described with reference to FIGS. 6A-6C. Graph 1200 shows a single accommodative response with a maximum amplitude of approximately 7 Diopters which was elicited by the accommodation stimulation device. The accommodative response was elicited and recorded over a period of 60 seconds.

FIG. 12B shows a graph 1220 depicting increased stimulus pulse-train durations, as delivered to the ciliary muscle to achieve the accommodative response. The stimulus pulse-train duration was approximately 60 seconds. The electrical stimulus was delivered at an intermediate stimulus amplitude of 30% of the maximum possible and a constant frequency of 200 Hz, as described with reference to FIG. 1C.

FIG. 12C is a graph 1240 depicting the velocities of the accommodative responses stimulated by the accommodation stimulation device. Velocities shown here were calculated from the accommodative responses described with reference to FIG. 12A. Shown here, the accommodations stimulation device can achieve an accommodative response over an extended period of time without significant change to the maximum accommodative response and without affecting the return to accommodative response baseline.

During some measurements, it may be beneficial to maintain an accommodation response for an extended period of time in order for a specific kind of measurement to be completed. For example, Magnetic Resonance Imaging (MRI) may take 15 to 20 seconds or greater periods of time, such as 45 seconds, to capture an image. As shown in FIGS. 12A-12C, the embodiments described herein can stimulate and maintain an accommodative response for these time durations or greater.

Figures 13A, 13B:
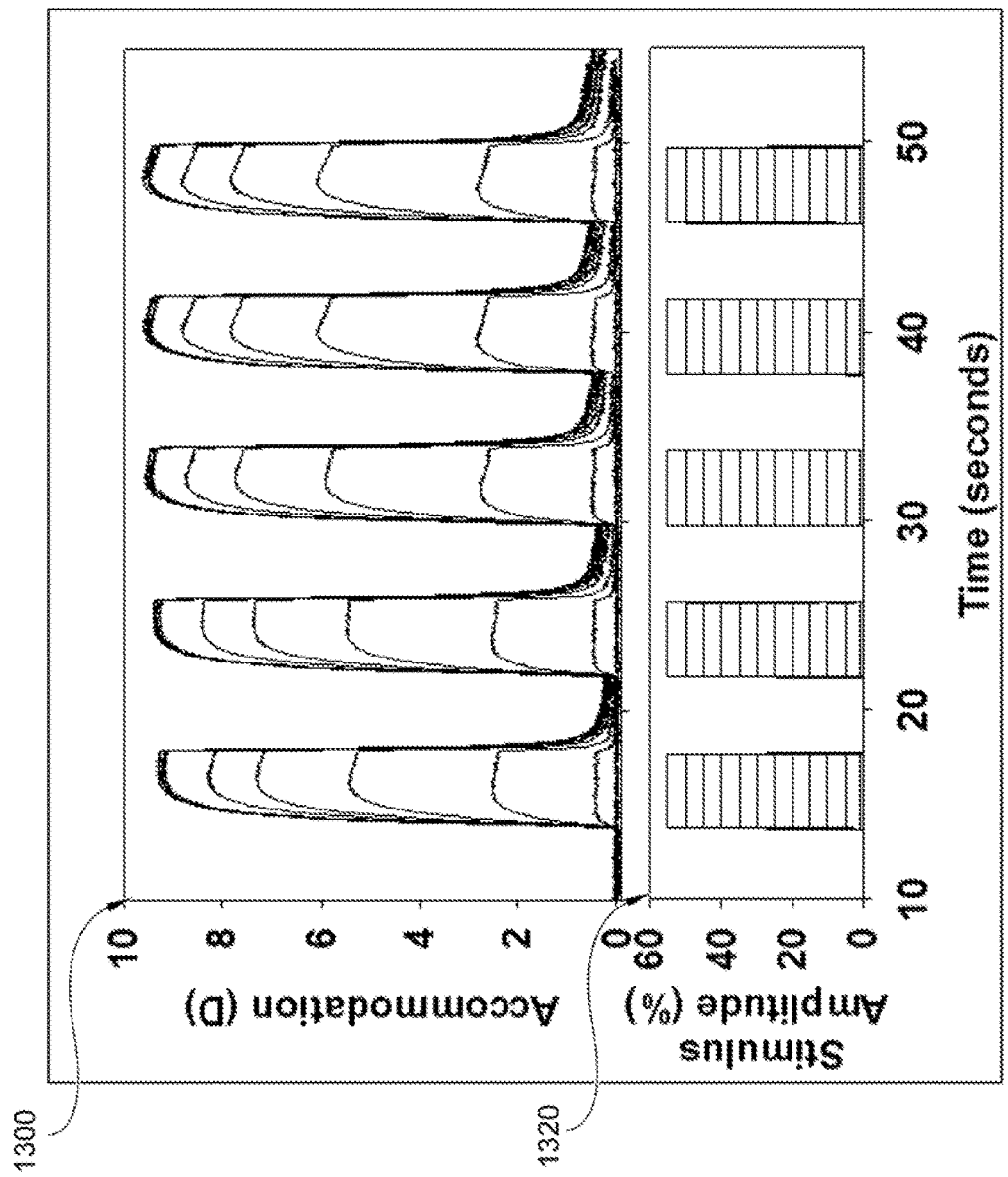
FIGS. 13A and 13B depict an overlay of stimulated accommodation responses with progressively increasing amplitudes, according to an embodiment.

FIGS. 13A and 13B depict an overlay of stimulated accommodation responses with progressively increasing amplitudes, according to an embodiment. FIG. 13A is a graph 1300 showing progressively increasing amplitude of accommodative response in response to an increasing stimulus amplitude as a percent (%) of maximum amplitude, shown in graph 1320 of FIG. 13B.

Graph 1300 and graph 1320 show that progressively increasing the stimulus amplitude from 0% to 55% in 12 steps increases the response amplitude from zero Diopters to the maximum accommodative response amplitude of about 9 Diopters. Shown in graph 1320, a total of twelve stimulus amplitudes, shown here at 2%, 5%, 10%, 15%, 20%, 25%, 30%, 35%, 40%, 45%, 50% and 55% are delivered to the ciliary muscle in the eye. For each stimulus amplitude, shown in FIG. 13B, five stimulus pulse-trains of 4 seconds each are delivered. The accommodative response amplitude, shown in graph 1300, progressively increases and ultimately reaches an asymptote for each of the 5 stimulus pulse-trains. The first seven amplitudes of the 12 stimulus amplitudes are visible presenting an accommodative response amplitude of about zero Diopters for the 0% and 5% stimulus amplitudes, about 0.5 Diopters for the 10% stimulus amplitude, about 2 Diopters for the 15% stimulus amplitude, about 6 Diopters for the 20% stimulus amplitude, about 7 Diopters for the 25% stimulus amplitude, about 8 Diopters for the 30% stimulus amplitude and about 9 Diopters for the 35% stimulus amplitude. The responses to the higher stimulus amplitudes still produce the same maximum accommodative responses of approximately 9 Diopters. The maximum accommodative response is expected to increase or decrease based on the accommodative capability of the eye.

Figure 14A:
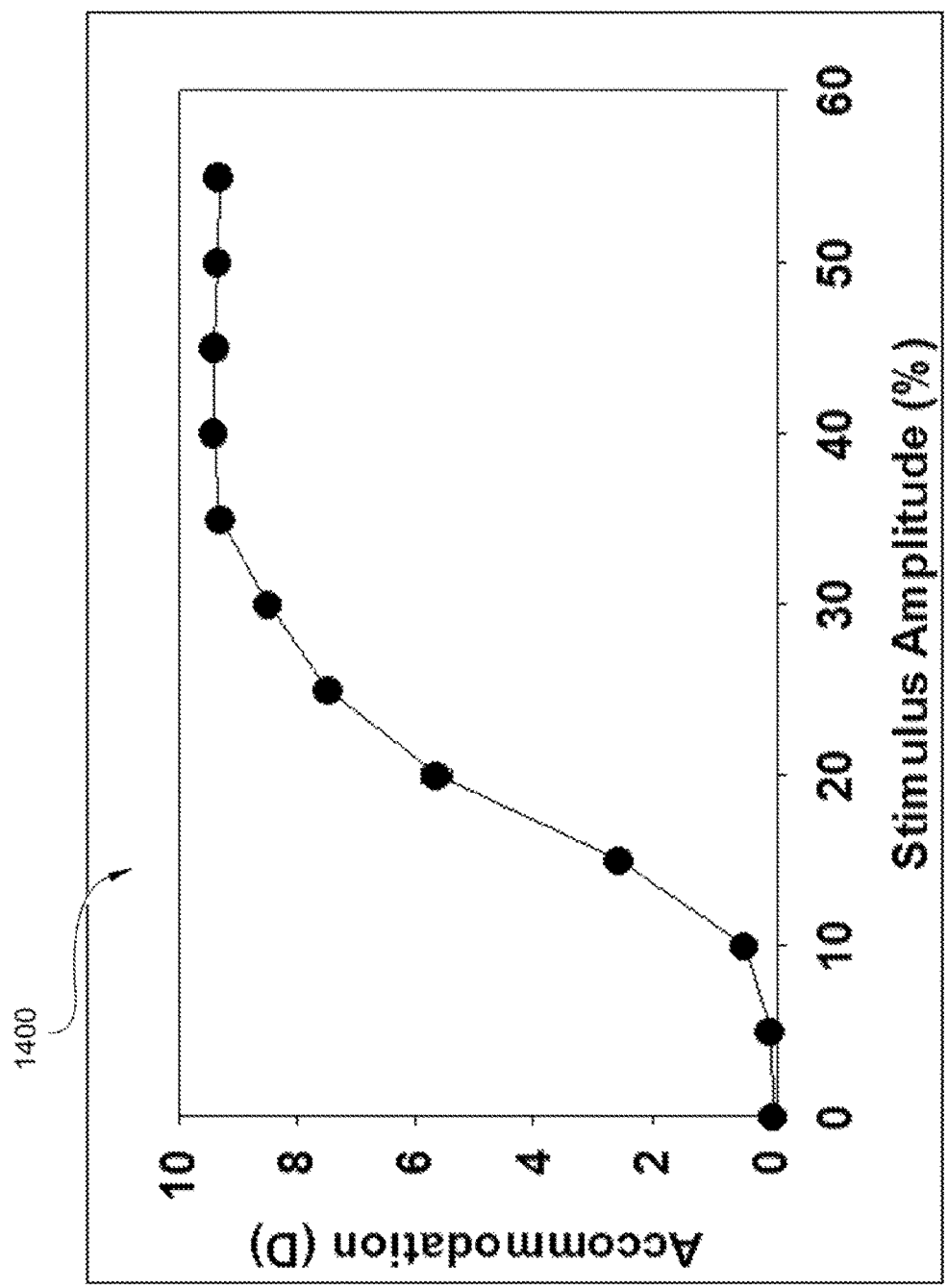
FIG. 14A is a graph depicting a typical stimulus response relationship for increasing stimulus amplitudes according to an embodiment.

FIG. 14A is a graph 1400 depicting a typical stimulus response relationship for increasing stimulus amplitudes according to an embodiment. The stimulus amplitudes shown in graph 1400 increase from 0% to 55%. As shown in the accommodative response data from FIG. 13A, the maximum accommodative response amplitude for this eye is approximately 9 Diopters.

In graph 1400, the maximum response occurs for a stimulus amplitude of about 35%. Increasing the stimulus amplitude further results in no further increase in response amplitude. Using the accommodation stimulation devices described herein, the maximum accommodative response amplitude available to any given eye can be determined by progressively increasing the stimulus amplitude until an asymptote is achieved. In addition, the stimulus amplitude required to achieve a specific accommodative response amplitude up to and including the maximal response can also be determined. For example, if an accommodative response of 6 Diopters is desired, then a stimulus amplitude of 20% should be used based on the data collected for this subject.

Figure 14B:
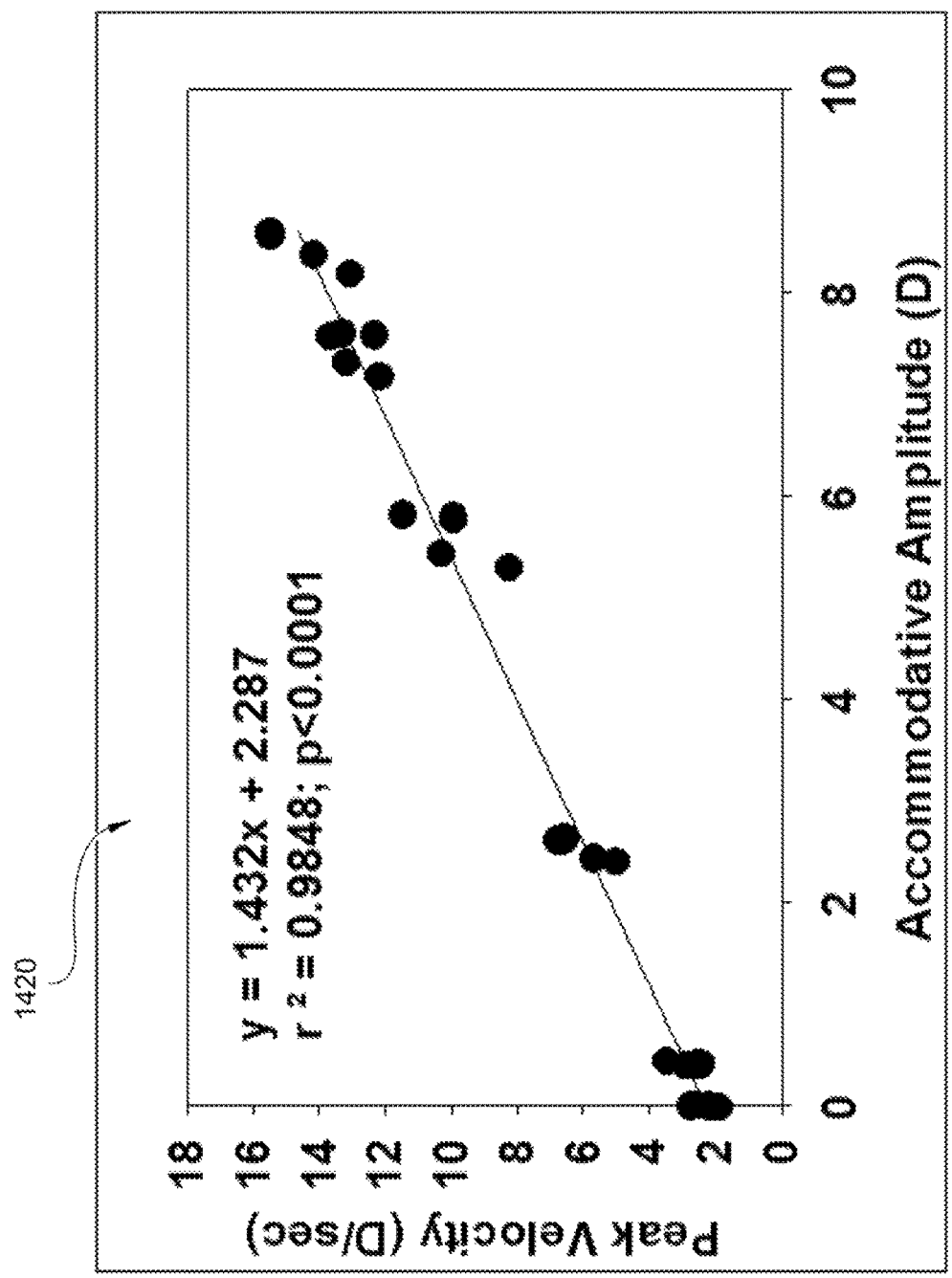
FIG. 14B is a graph depicting peak velocity as a function of accommodative amplitude according to an embodiment.

FIG. 14B is a graph 1420 depicting peak velocity as a function of accommodative amplitude according to an embodiment. Graph 1420 depicts the velocity of the accommodative response as derived from the accommodative response data from FIG. 13A at the stimulus amplitudes depicted in FIG. 13B. The velocity of the accommodative response is plotted against the maximum accommodative response amplitude for the same accommodative responses. Graph 1420 shows that as the stimulated accommodative amplitude increases, the peak velocity of the accommodative response increases linearly. As stimulated accommodative response amplitude has been shown to be directly correlated to stimulus amplitude, increasing stimulus amplitude as delivered through the accommodation stimulation device, described above with reference to FIGS. 1A-1C, leads to an increase in the peak velocity of the stimulated accommodative response.

Therefore, the accommodation stimulation device is capable of both controlling the accommodative amplitude and the velocity of accommodation in the user. It is envisioned that a stimulus pulse-train delivered through the accommodation stimulation device could have steps in the amplitude such that the velocity is controlled independent of the maximum accommodative response achieved. For example, a stimulus pulse-train could begin at a high amplitude which is subsequently reduced to a medium amplitude, selected to choose a specific maximum accommodative response amplitude. One skilled in the art will understand that there are a plurality of possible combinations which could be performed based on the disclosures described herein.

FIGS. 15A-15C depict a plurality of stimulated accommodative responses with progressively decreasing frequencies using the device described above with reference to parameters described in FIGS. 6A-6C. FIG. 15A is a graph 1500 of elicited and measured accommodative responses over an extended period of time. The accommodative responses were produced by electrical stimulation, shown with reference to graph 1520 of FIG. 15B.

Accommodative responses were stimulated using the accommodation stimulation device described with reference to FIGS. 1A-1C and using parameters described with reference to FIGS. 6A-6C. Graph 1500 shows 16 individual accommodative responses with a progressively decreasing accommodative response amplitude, which were elicited by an accommodation stimulation device described with reference to FIGS. 1A-1C. The accommodative responses were elicited and recorded over a period of 230 seconds.

The first accommodation response is approximately 6 Diopters which is maintained in the first five accommodation responses. Beginning with the sixth accommodation response, the maximum amplitude begins to decrease. The sixth accommodation response has a maximum amplitude of approximately 5.5 Diopters. The seventh accommodation response has a maximum amplitude of approximately 5 Diopters. The eighth accommodation response has a maximum amplitude of approximately 4.5 Diopters. The ninth accommodation response has a maximum amplitude of approximately 4 Diopters. The tenth accommodation response has a maximum amplitude of approximately 4 Diopters. The eleventh accommodation response has a maximum amplitude of approximately 2 Diopters. The twelfth through sixteenth accommodation responses have maximum amplitudes of approximately 1 Diopters or less, with a progressive decrease from the twelfth through the sixteenth.

Embodiments described herein include methods for rapidly determining the maximum accommodative amplitude of the eye. With electrical stimulated accommodation, the amplitude of the accommodative response can be controlled by either adjusting the current amplitude of the stimulus or by adjusting the frequency of the stimulus pulses delivered to the eye. Typically clinical methods for objectively measuring accommodation to determine the maximum accommodative amplitude of an eye can be very laborious and can be a very demanding task for the patient which can take many minutes to perform. Because of the lengthy duration of testing required, this can result in fatigue to the patient which thereby results in a failure of the patient to elicit the maximum accommodative amplitude. The electrical stimulation of accommodation with a progressively increasing amplitude of the electrical stimulus or a progressively increasing frequency of the electrical stimulus pulses can provide a method for determining the maximum accommodative amplitude available to the eye in a very short period of for example 30 seconds to one minute.

This method of electrically stimulating accommodation includes a method whereby the electrical stimulus to the eye could be controlled and delivered by the same instrument that is used to measure the accommodative response. When the eye accommodates, there is an optical change in the refraction of the eye which is caused by the physical or biometric movements of the lens inside the eye. Instruments that can be used to measure the optical refractive accommodative response of the eye include instruments such as an autorefractor, an aberrometer or a photorefractor. Instruments that can measure the biometric accommodative response of the eye include instruments such as Optical Coherence Interferometers (OCT), Ultrasound Biomicroscopes (UBM), Magnetic resonance imaging instruments (MRI). Any instrument that can measure the accommodative response of the eye is referred to here as an ocular measurement instrument. Ocular measurement instruments are generally controlled by a microprocessor, such as an external computer or an internal microcontroller or microprocessor. The same microprocessor and its associated software that is used to operate the ocular measurement instrument could also be used to control and deliver the electrical stimulus to the eye. This combination of both stimulating accommodation and measuring of the accommodative response of the eye with the same instrument allows for a feedback-control loop that would facilitate a very rapid determination of the maximum accommodative response of the eye. The software controlling the ocular measurement instrument could rapidly run through a sequence of stimulations of increasing stimulus amplitudes or a sequence of increasing stimulus frequencies while the ocular measurement instrument also simultaneously measures the accommodative response of the eye. The stimulation and measurement sequence would continue until the ocular measurement instrument had determined that the maximum accommodative response of the eye had been achieved. In this manner, the process of determining the maximum accommodative amplitude could be achieved very rapidly, such as within seconds.

FIG. 15B shows a graph 1520 depicting constant stimulus pulse-train durations, as delivered to the ciliary muscle to achieve the accommodative response, with progressively decreasing stimulus pulse-train frequencies. The stimulus pulse-train durations were approximately 4 seconds. The stimulated accommodative responses depicted were stimulated at an intermediate stimulus amplitude of 30% of the maximum possible with a steadily decreasing stimulus frequency. The stimulus frequency was progressively decreased from the first stimulus pulse-train to the sixteenth stimulus pulse-train. Together, graph 1500 and graph 1520 demonstrate that the frequency of the stimulus pulse-train can be used to change the accommodative response amplitude.

FIG. 15C is a graph 1540 depicting the velocities of the accommodative responses stimulated by the accommodation stimulation device. Velocities shown here were calculated from the accommodative responses described with reference to FIG. 15A. As shown here, the stimulation and relaxation velocities of the accommodative responses decrease as the accommodative response amplitudes decrease. This decrease in stimulation and relaxation velocities is in accordance with what occurs when different accommodative response amplitudes are achieved by stimulating the ciliary muscle using different stimulus amplitudes, but with a constant pulse-train frequency.

Figure 15D:
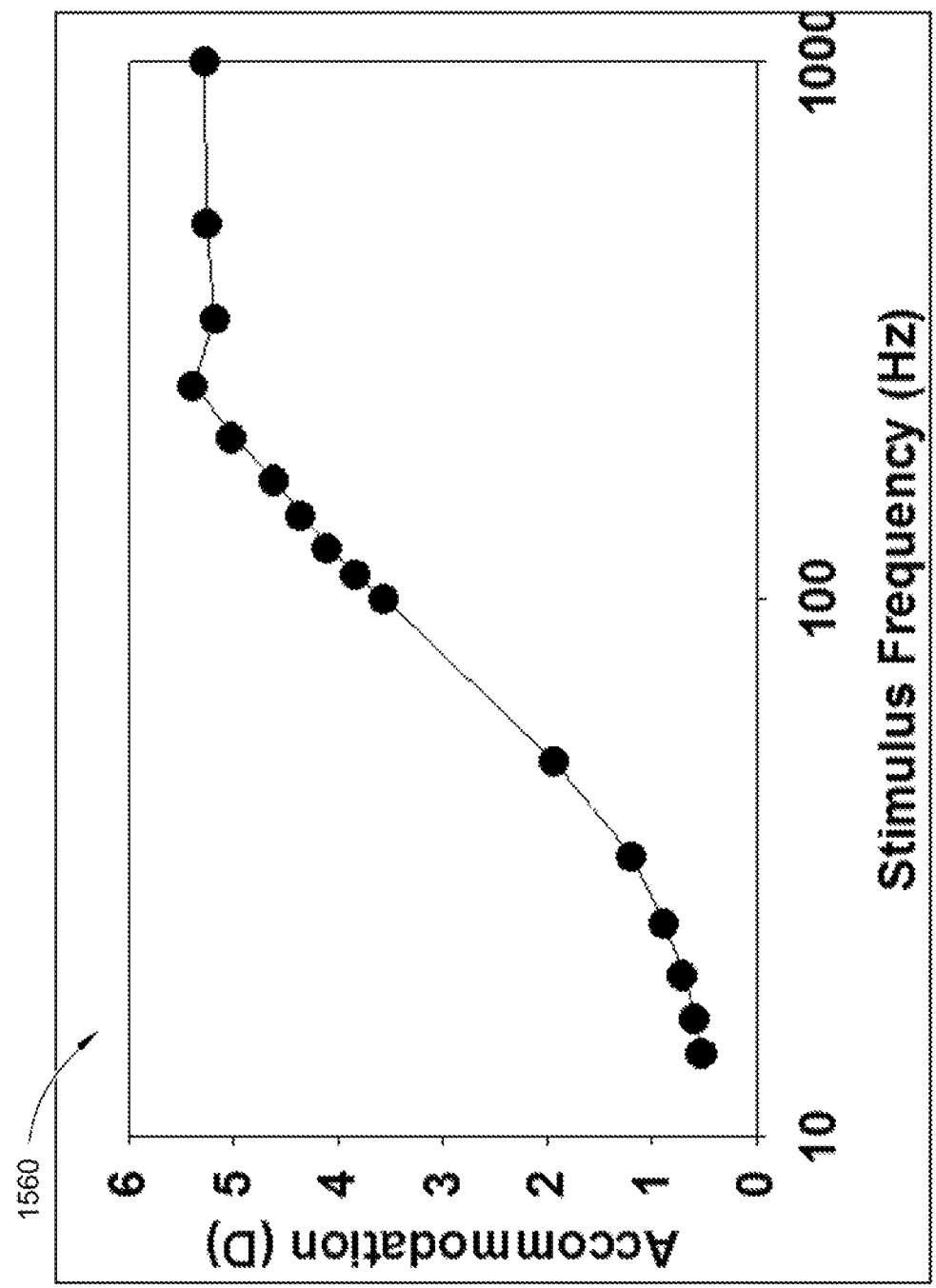
FIG. 15D is a graph depicting the accommodative response amplitudes achieved for stimulus pulse-trains with constant amplitude and variable frequency according to an embodiment.

FIG. 15D is a graph 1560 depicting the maximum accommodation amplitude for stimulus pulse-trains with constant amplitude and variable frequency as described with reference to FIG. 15A-15C. This graph 1560 shows the maximum amplitude of the accommodative responses as depicted in graph 1500 of FIG. 15A. Graph 1560 shows that as stimulus pulse-train frequency increases with a constant fixed amplitude stimulus, accommodative response amplitude increases to an asymptote of in this case about 5.5 Diopters.

It is believed that an optimal pulse train frequency is required to achieve the maximum accommodative response amplitude. As shown here, the stimulus pulse train frequency of between 200 Hz and 1000 Hz achieved the maximum accommodative response of this eye. As a certain level of variability is expected from one eye to the next, the maximum accommodative amplitude available to any given eye can be determined by progressively increasing the stimulus frequency until an asymptote is achieved.

Using the maximum accommodation response amplitude as compared to the stimulus frequency, the stimulus frequency required to achieve a specific accommodative response up to the maximum accommodative response can also be determined. For example, in one embodiment, if an accommodative response of 2 Diopters is desired, then a stimulus frequency of 50 Hz should be used.

Figure 15E:
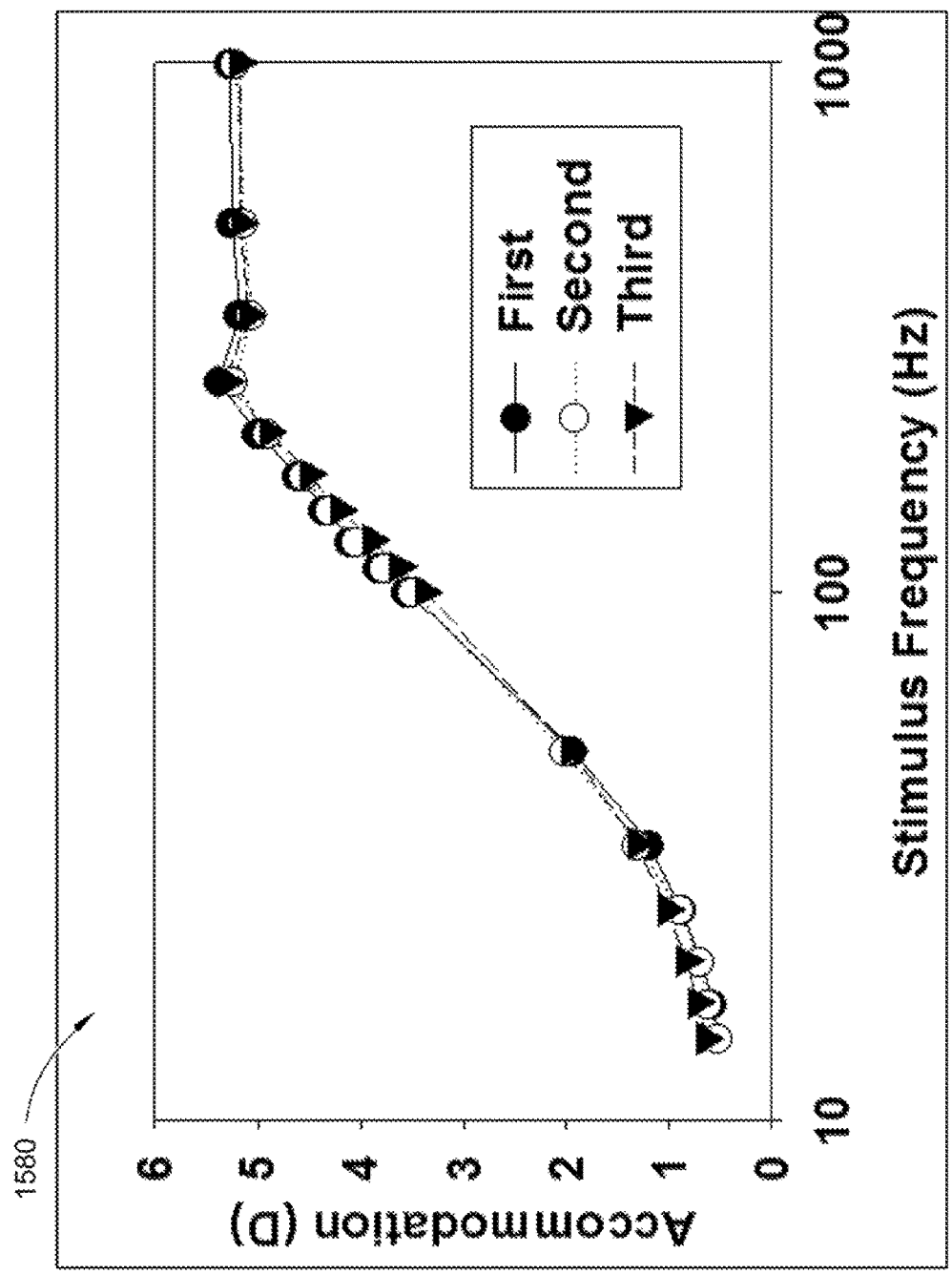
FIG. 15E is a graph depicting the accommodative response amplitudes achieved from three sets of measurements for stimulus pulse-trains with constant amplitude and variable frequency according to an embodiment.

FIG. 15E is a graph 1580 depicting the maximum accommodation amplitude from three sets of measurements for stimulus pulse-trains with constant amplitude and variable frequency as described with reference to FIG. 15A-15C. Graph 1580 shows the results from three repeats of increasing stimulus pulse-train frequency (shown here as First, Second and Third) on the same eye. The amplitude was maintained constant as the frequency was varied as described in FIGS. 15A-15C. Graph 1580 shows that the stimulation accommodation device produces consistent results at a various stimulus frequencies.

As above, it is envisioned that a stimulus pulse-train delivered through the accommodation stimulation device could have steps in the frequency such that the velocity is controlled independent of the maximum accommodative response achieved. For example, a stimulus pulse-train could begin at a high frequency and a constant amplitude which is subsequently reduced to a medium frequency and a constant amplitude, selected to choose a specific maximum accommodative response amplitude. Frequency and amplitude steps described above could also be used in combination to achieve a variety of accommodative response velocities and peak accommodative response amplitudes.

Figure 16:
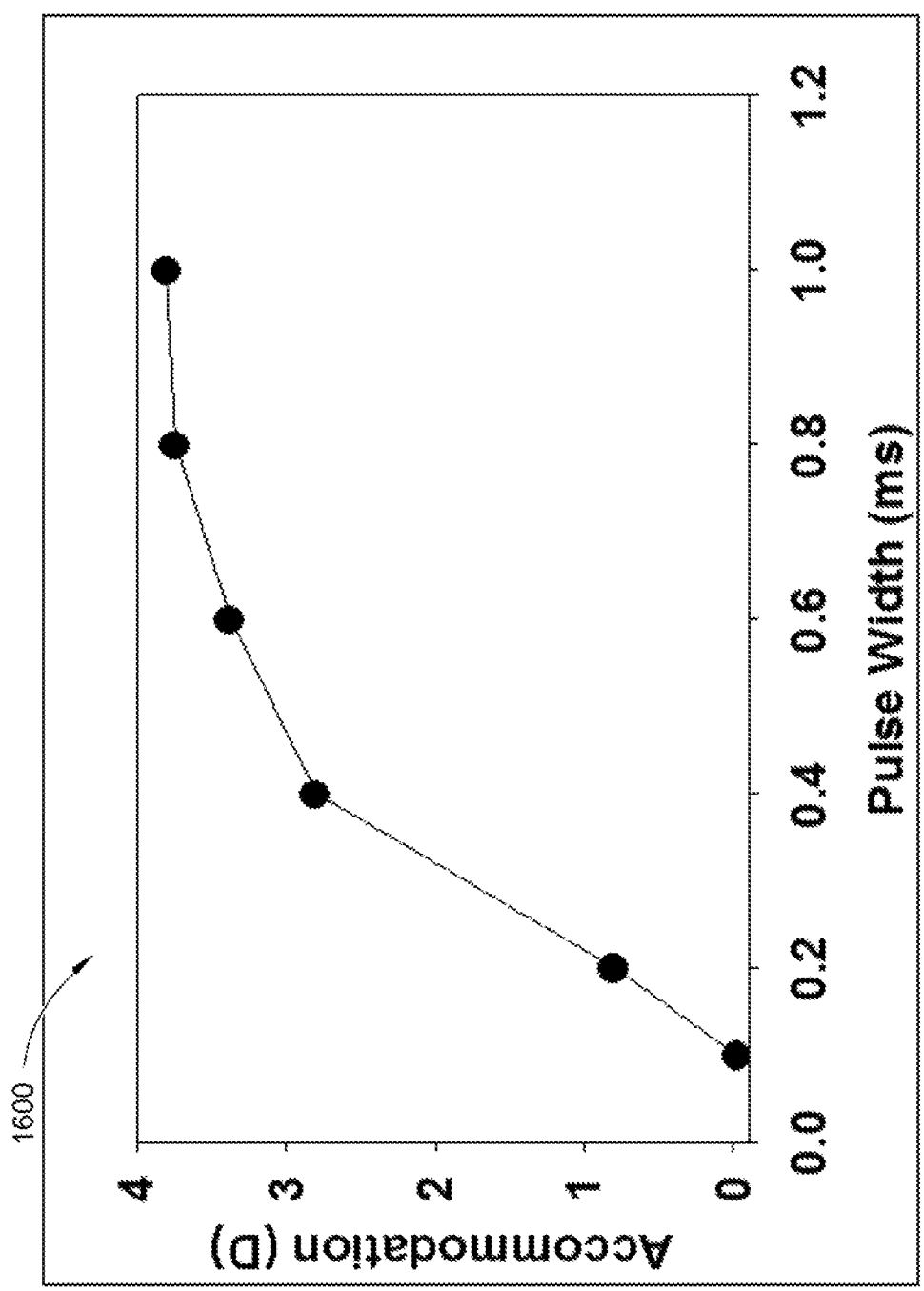
FIG. 16 is a graph depicting a plurality of accommodation responses in an eye using the accommodation stimulation device with a variable pulse width for the stimulus pulse-trains of constant amplitude and frequency according to an embodiment.

FIG. 16 is a graph 1600 depicting a plurality of accommodation responses in an eye using the accommodation stimulation device with a variable pulse width for the stimulus pulse-train according to an embodiment. The pulse width of the stimulus pulse train is the width of the plurality of pulses which form the stimulus pulse train. For example, a stimulus pulse train of 4 seconds can be composed of a plurality of individual pulses with a pulse width of between 100 μs and 10 ms. The number of pulses multiplied by the width of each pulse in addition to the spacing between pulses is equal to the stimulus pulse train.

The pulse-train pulse-width can be delivered at a variety of widths, as measured in millisecond (ms), such as from 0.1 ms to 1.0 ms. Though depicted here with a final pulse width of 1.0 ms, embodiments described herein are not limited to a pulse width of 1.0 ms. As the pulse width is increased towards 1 ms, the accommodative amplitude increases to an asymptote. Shown in graph 1600, the asymptote is approximately 4 Diopters. In embodiments described herein, pulse widths of about 800 microseconds (800 μs) or higher can be used to produce the desired accommodative response. Shown in FIGS. 14A, 15D and 16, the stimulus pulse-train amplitude, stimulus pulse-train frequency and stimulus pulse width can all be adjusted to regulate the accommodative response amplitude.

Figure 17A:
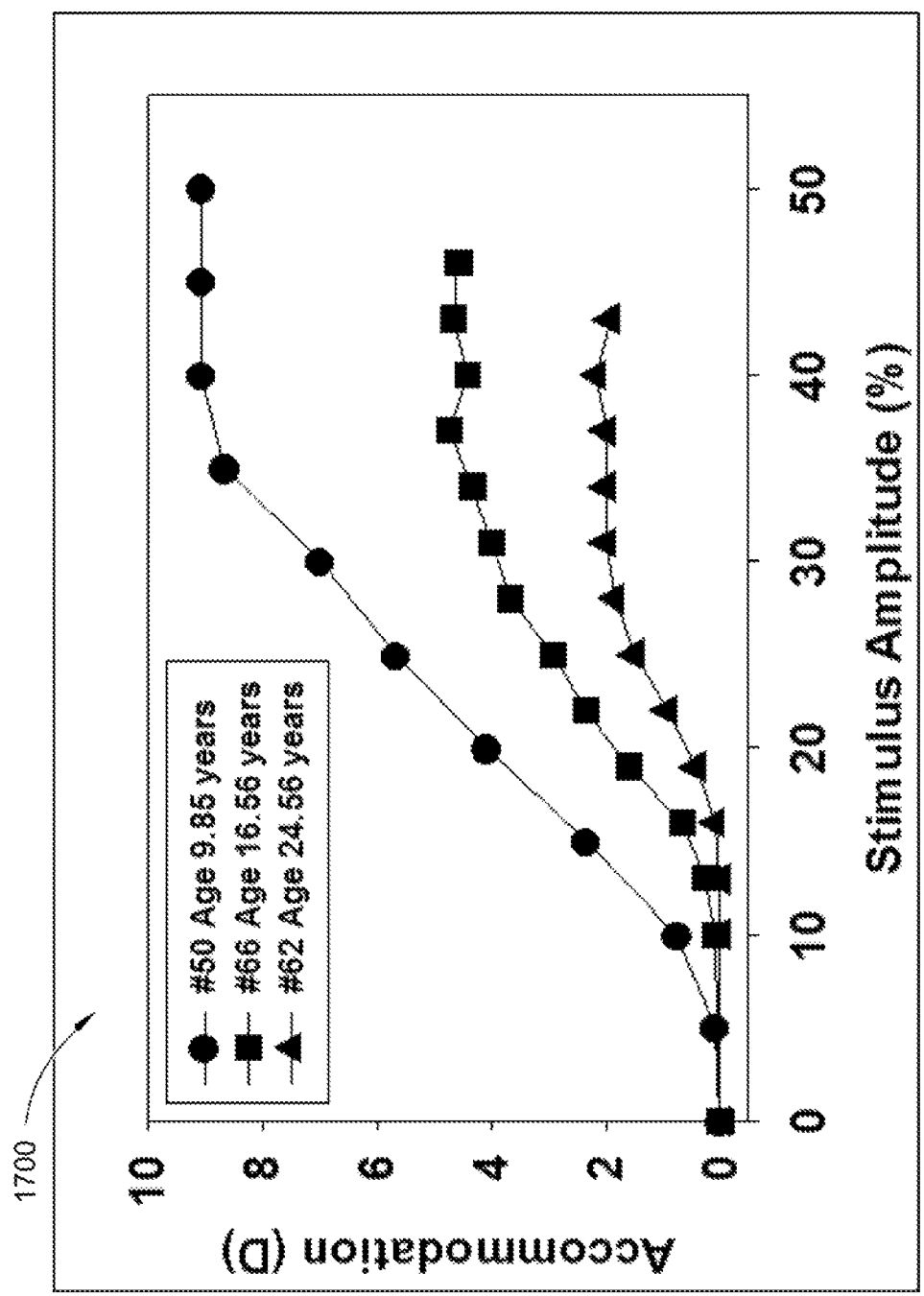
FIG. 17A is a graph depicting the maximum accommodative response for each stimulus amplitude for eyes of varying age stimulated by the accommodation stimulation device according to an embodiment.

FIG. 17A is a graph 1700 depicting the maximum accommodative response for each stimulus amplitude for eyes of varying age stimulated by the accommodation stimulation device according to an embodiment. The accommodation stimulation device used in graph 1700 is the accommodation stimulation speculum described in more detail with reference to FIGS. 1A-1C. Graph 1700 shows three stimulus response functions as described with reference to FIG. 14A. Graph 1700 depicts the stimulus response functions for three monkeys of differing ages with the youngest at 9.85 years old (#50), the intermediate monkey at 16.56 years old (#66) and the oldest monkey at 24.56 years old (#62). Graph 1700 shows that, with increasing age, the accommodative response amplitude progressively decreases. Monkey #50 shows a maximum accommodative response of approximately 9 Diopters which is achieved by a stimulus amplitude of about 35% of the maximum amplitude. Monkey #66 shows a maximum accommodative response of approximately 4.5 Diopters which is achieved by a stimulus amplitude of about 35% of the maximum amplitude. Monkey #62 shows a maximum accommodative response of approximately 2 Diopters which is achieved by a stimulus amplitude of about 30% of the maximum amplitude. In each eye, the maximum accommodative response amplitude attainable for that eye is achieved with the increasing stimulus response functions.

Figure 17B:
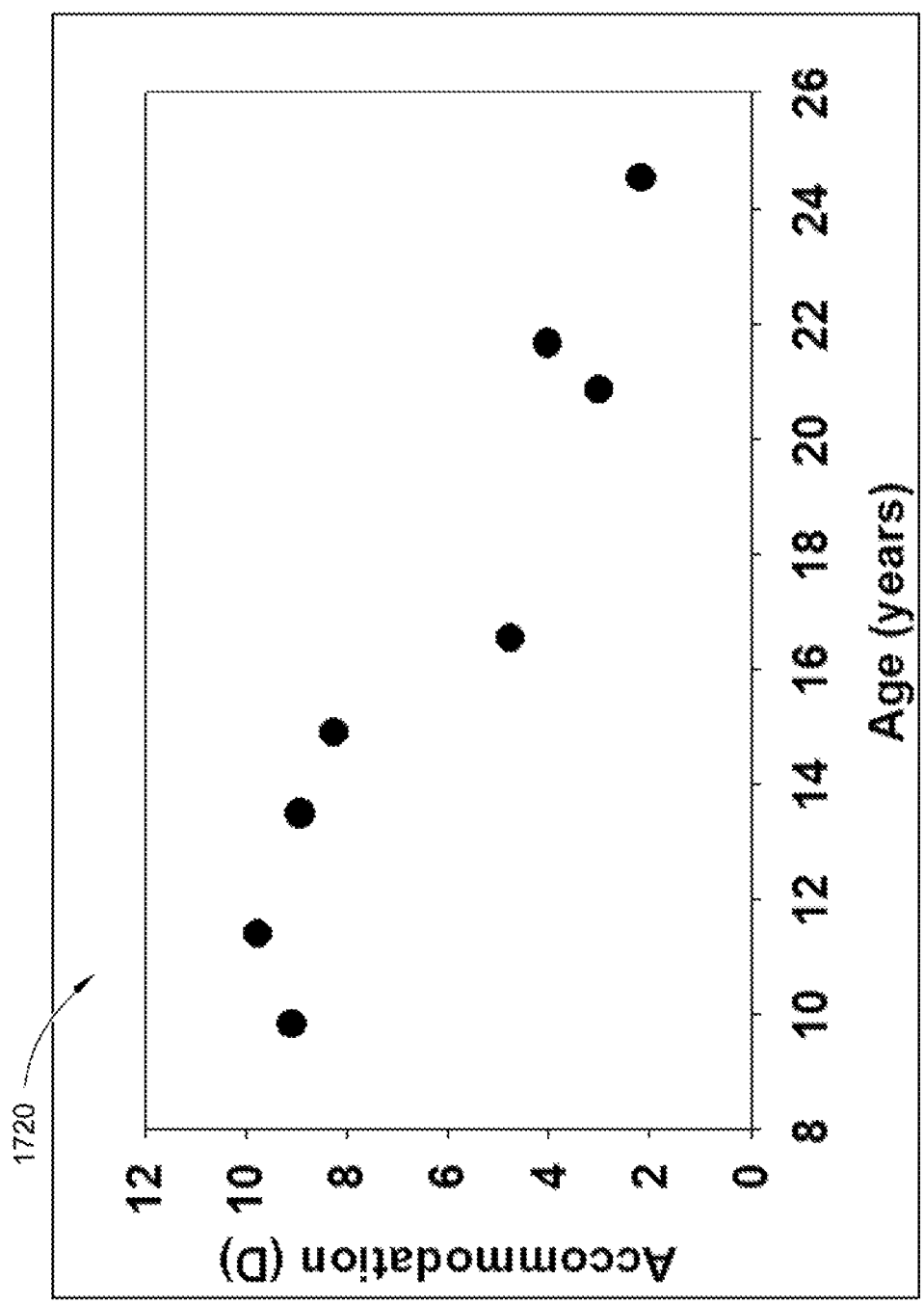
FIG. 17B is a graph depicting the maximum accommodative response amplitude in eight monkeys of differing ages achieved using an accommodation stimulation device according to an embodiment.

FIG. 17B is a graph 1720 depicting the maximum accommodative response in eight monkeys of differing ages achieved using an accommodation stimulation device according to an embodiment. The accommodation stimulation device employed here is the accommodation stimulation speculum described with reference to FIGS. 1A-1C, which is used in conjunction with the stimulus pulse-train frequencies, amplitudes and pulse widths described with reference to FIGS. 14A, 15D and 16.

Shown in graph 1720, the maximum accommodative response achievable by the accommodation stimulation device is diminished based on age. Between the ages of about 9 years old and about 15 years old, maximum accommodative response shown here ranges between 8 and 10 Diopters. In these monkeys, the accommodative response peaks at approximately 10 Diopters in the approximately 11 year old monkey. A sharp drop in maximum accommodative response was seen between the approximately 14 year old monkey and the approximately 17 year old monkey to about 4 Diopters. Between the approximately 17 year old monkey and the approximately 25 year old monkey the decline in maximum accommodative response was steady from about 4 Diopters to about 2 Diopters. Thus graph 1720 shows that accommodative response can be achieved reliably in various age groups, even considering age-related decline in accommodative response capability.

Fabrication Methods

Figure 18:
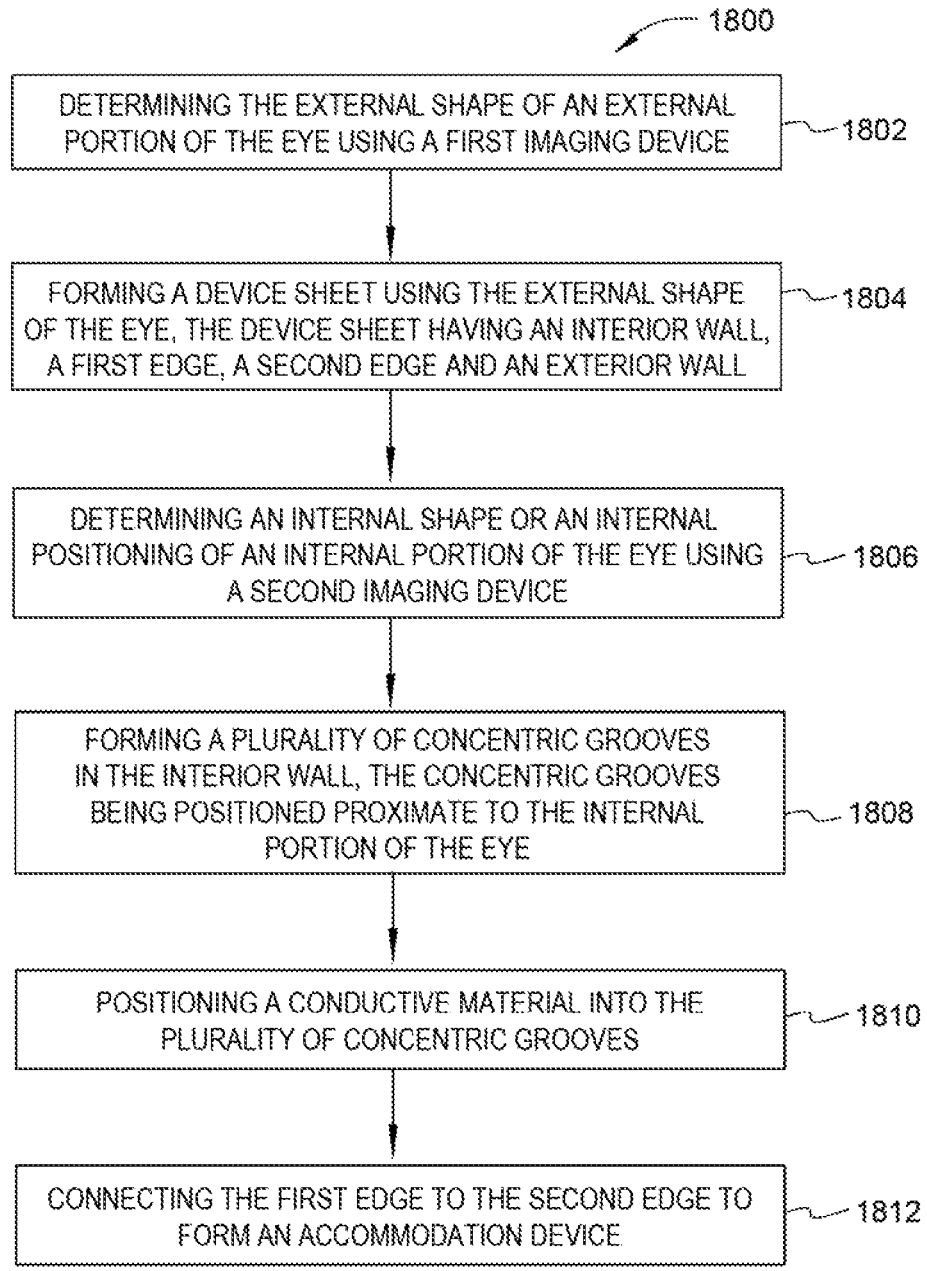
FIG. 18 depicts a method of fabricating an accommodation device, according to an embodiment.
Figure 19A:
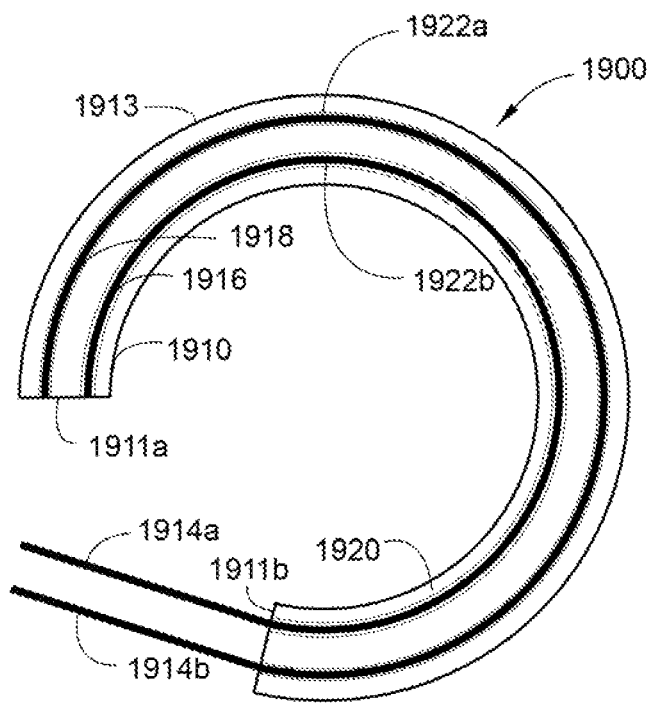
FIG. 19A depicts an accommodation stimulation scleral annulus 1900 cut according to an embodiment.
Figure 19B:
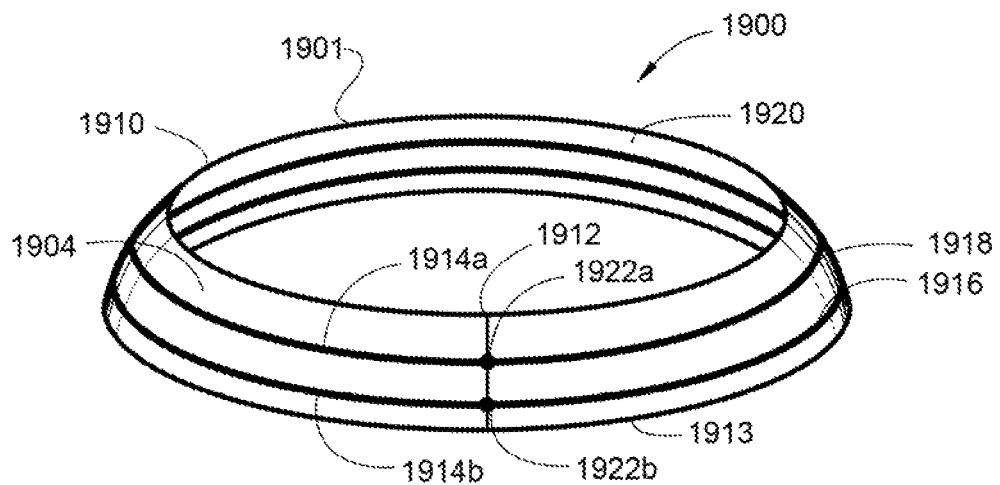
FIG. 19B depicts the accommodation stimulation scleral annulus 1900 formed according to an embodiment.

FIGS. 18 and 19A-19B depict an accommodation stimulation device according to one or more embodiments and methods of forming the same. By determining the internal and external shape of the eye, the electrodes can be positioned more precisely and with better contact to the eye, such that the stimulation may be delivered more precisely and with more energy efficiency.

FIG. 18 depicts a method of fabricating an accommodation device, according to an embodiment. The method 1800 can begin by determining the external shape of an external portion of the eye using a first imaging device, at element 1802. Determining the external shape can include using ocular imaging methods to measure the external shape of the front of the eye to enable construction of an electrode that provides an ideal fit to the eye. Imaging methods which may be employed with one or more embodiments of the invention include Optical Coherence Tomography (OCT), Ultrasound Biomicroscopy (UBM) or Magnetic Resonance Imaging (MRI). The above imaging methods may provide either 2D or 3D images of the eye that can be used to define best fit of the electrode to each individual eye, thereby customizing the fit of the electrode to the sclera overlying the ciliary muscle.

A device sheet is then formed using the external shape of the eye, the device sheet having an exterior wall, a first edge, a second edge and an interior wall, at element 1804. The device sheet may be formed by cutting, melting, ablating, etching or other techniques. When formed by cutting, the device can be cut on a contact lens lathe. The device sheet can be formed of standard contact lens materials, such as polymethyl methacrylate (PMMA). In one embodiment, the contact lens lathes receives a data file from a user that describes the parameters of the surfaces to be cut. The data file can incorporate both user specification and information from the ocular imaging described above. Using this input, one surface can be cut from a button of the desired material. This button with one cut surface is then detached, turned around, remounted on the lathe and then the second surface is cut. A method for fabricating the electrode may also include cutting concentric grooves in the inner surface of the electrode using a contact lens lathe to create grooves into which the electrode conductive wires can be set and glued into place.

An internal shape or an internal positioning of an internal portion of the eye can then be determined using a second imaging device, at element 1806. Some of these imaging methods also allow visualization of the internal portions of the eye, such as the ciliary muscle. This imaging can be performed using the same device or technique as the external imaging or using a separate device or technique. This information can be employed in the design of electrodes to ensure that the electrical contacts of the conductive elements of the electrode are optimally positioned with respect to the location of the ciliary muscle within the eye.

A plurality of concentric grooves can then be formed in the interior wall, at element 1808. In one embodiment, the imaging of the ciliary muscle is employed to position the concentric grooves proximate to the ciliary muscle of the eye. The electrode can comprise at least a negative (anode) and a positive (cathode) electrode. The electrodes can be configured into two concentric rings. Each of the anode and cathode can include a single conductive wire, or each of the anode and cathode can include a set of conductive wires, each being comprised of two or more smaller diameter wires. Each of the cathode and the anode can include a single sheet of conductive material, such as a wire which is formed in a deposition procedure on a printed circuit board.

The conductive material can then be positioned into the plurality of concentric grooves, at element 1810. A method of fabrication of the electrode can include printing electrodes with conductive material on a flat, but moldable circular or annular shaped plastic material. The plastic material can be molded with heated or pressurized forces to mold the material into the shape of a contact lens or an annulus that would fit on the eye.

The first edge can then be connected to the second edge to form an accommodation device, at element 1812. A method of fabrication of the electrode includes creating an annulus from a flattened sheet of material with the conductive wires laid down and adhered to the flattened sheet. The edges of the flattened sheet could then be joined, such as by gluing or adhering them together, to form the annulus. In one embodiment, the conductive material may be protruding through the joined ends of the annulus.

FIGS. 19A and 19B depict an accommodation stimulation scleral annulus 1900 fabricated according to an embodiment. FIG. 19A depicts an accommodation stimulation scleral annulus 1900 cut according to the method described in FIG. 18. The accommodation stimulation scleral annulus 1900 is shown here as a flat sheet from the view of a posterior surface (inner wall) 1920, with an opening 1910, an outer ring 1913, a first edge 1911a and a second edge 1911b. Traces 1922a and 1922b are formed in the posterior surface 1920. The traces 1922a and 1922b can then receive the conductive material to form an inner ring electrode 1916 and an outer ring electrode 1918. The inner ring electrode 1916 and the outer ring electrode 1918 have electrode extensions 1914a and 1914b respectively.

FIG. 19B depicts the accommodation stimulation scleral annulus 1900 formed according to the method described in FIG. 18. The accommodation stimulation scleral annulus 1900 is depicted with an annulus body 1901 which substantially conforms to the shapes and curvatures of the eye (not shown). The annulus body 1901 can be composed of a material such as those used in conjunction with the accommodation stimulation speculum 100 or the accommodation stimulation scleral contact lens 200, described with reference to FIGS. 1 and 2 respectively.

An opening 1910 is formed in the annulus body 1920 which circumscribes the cornea of the eye. The annulus body 1901 has an anterior surface (outer wall) 1904 and the posterior surface 1920. The posterior surface 1920 rests above or on the sclera of the eye such that an outer ring electrode 1916 and an inner ring electrode 1918 are brought in electrical contact with the sclera. As above, the outer ring electrode 1916 and the inner ring electrode 1918 are positioned over a region of the sclera which corresponds to the area of the underlying ciliary muscle. The annulus body 1910 can be of an approximately equal width, as depicted, and can be sized to appropriately correspond to the eye of the user.

The first edge 1911a and the second edge 1911b are then joined to form a connection 1912 with holes 1922a and 1922b. The electrode extensions 1914a and 1914b can extend through holes 1922a and 1922b respectively. The electrode extensions 1914a and 1914b can be used to form the first connection 106 and the second connection 108, as shown with relation to the accommodation stimulation speculum 100 of FIGS. 1A and 1B.

In another embodiment, a method of fabrication of the electrode can include creating a mold such as an injection mold. The mold can receive a liquid, such as a liquid polymer or silicone, which is poured or injected into the mold. When the liquid sets or polymerizes, the annulus or lens can be removed from the mold ready to be placed on the eye. Such a mold could have grooves formed into one surface, which can receive the conductive wires. The wires can be integrated into the mold, such that when the liquid silicone or polymer is set and the set polymer removed, the wire electrodes would be partially embedded in the set polymer or silicone. A method of fabrication of the electrode can also include modeling the form of the electrode in 3D computer aided design (CAD) software and then 3D printing the annulus in a biocompatible material.

Radio Frequency (RF) Wireless Control

In its current formulation, the electrode has electrically conductive wires that connect the stimulator that delivers the electrical stimulus to the electrode on the eye. These conductive wires carry the current from the stimulator to the eye. It is possible that the electrical stimulus could be delivered wirelessly with radio frequencies (RF) from an RF transmitter on the stimulator to a RF receiver located on the electrode. The electrode on the eye would need to have an RF receiver, a microcontroller and a power source. When the wirelessly transmitted stimulus is received, that signal would be interpreted and then the electrical stimulus would be delivered from the power source. This would allow the patient to wear the electrode more comfortably on the eye without the need to have electrically conductive wires to the electrode on the eye.

Figure 20:
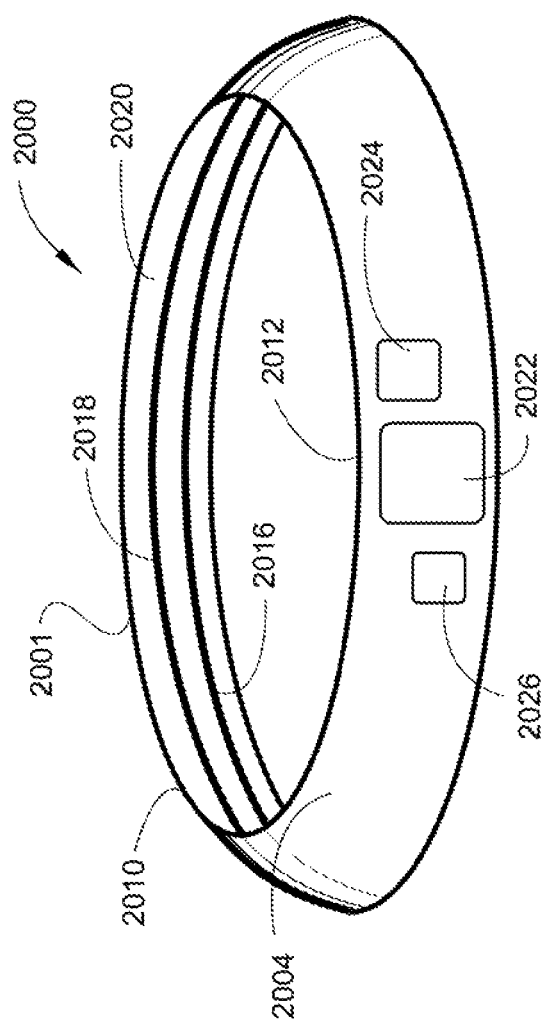
FIG. 20 depicts the accommodation stimulation scleral annulus 2000 including an RF transmitter 2022 according to one embodiment.

FIG. 20 depicts the accommodation stimulation scleral annulus 2000 including an RF transmitter 2022 according to one embodiment. The accommodation stimulation scleral annulus 2000 is depicted with an annulus body 2001 which substantially conforms to the shapes and curvatures of the eye (not shown). The annulus body 2001 can be composed of a material such as those used in conjunction with the accommodation stimulation speculum 100 or the accommodation stimulation scleral contact lens 200, described with reference to FIGS. 1 and 2 respectively.

An opening 2010 is formed in the annulus body 2020 which circumscribes the cornea of the eye. The annulus body 2001 has an anterior surface (outer wall) 2004 and a posterior surface (inner wall) 2020. The posterior surface 2020 rests above or on the sclera of the eye such that an outer ring electrode 2016 and an inner ring electrode 2018 are brought in electrical contact with the sclera. As above, the outer ring electrode 2016 and the inner ring electrode 2018 are positioned over a region of the sclera which corresponds to the area of the underlying ciliary muscle. The annulus body 2010 can be of an approximately equal width, as depicted, and can be sized to appropriately correspond to the eye of the user.

The accommodation stimulation scleral annulus 2000 further includes an RF transmitter 2022, a microprocessor 2024 and a power supply 2026. The microprocessor 2024 receives one or more signals.

For the electrode on the eye that is used to record the accommodative contraction of the ciliary muscle, normally, this would be accomplished by connecting electrically conductive material from the accommodation stimulation scleral annulus 2000 on the eye to the preamplifier (not shown). The preamplifier would amplify the recorded muscle potentials in order to record them. However, using a RF transmitter 2022 on the accommodation stimulation scleral annulus 2000, the recorded potentials could be wirelessly transmitted from the accommodation stimulation scleral annulus 2000 on the eye to the preamplifier and recorder. This would allow the ciliary muscle activity that occurs with accommodation to be recorded wirelessly.

Allowing both accommodation stimulation to be delivered wirelessly and accommodative ciliary muscle contractions to be recorded wirelessly would mean that the stimulating electrode or the recording electrode could be more comfortably and more functionally worn on the eye for prolonged periods of time. This would facilitate everyday use of these accommodation stimulation devices and allow them to be maintained and used on the eye for daily activities, such as for remotely controlling the accommodative response of the eye while reading for prolonged periods of time, or for the remote monitoring of ciliary muscle function to provide feedback control of an electro-active polymer accommodative intraocular lens. A patient could wear the stimulation electrode on the eye and with a remote controlled device such as a smart phone or a smart tablet, initiate the delivery of a stimulus to the eye to allow the eye to change focus by a controlled amount so that the eye could maintain focus on an object that is at a certain distance from the eye. This would allow the user remote control or automated control of the accommodative response using RF wireless electrical stimulation. The smart phone in this instance could detect the distance of the device to the eye and deliver a stimulus of the appropriate magnitude to allow the eye to focus appropriately on the smartphone.

Pre-Operative Screening of Patients for Accommodative Function

The embodiments, as described above, can be used both in accommodation and detection of accommodation or attempted accommodation. Older patient populations, such as patients over the age of 50, may provide difficulties not seen in other patient populations, because some of them may not have experienced accommodation for some years. As such, conventional testing for accommodation in this group of patients is challenging.

It is believed that presbyopia results from an age-related stiffening of the presbyopic lens in the eye and that the ciliary muscle remains functional throughout life, including beyond the age at which accommodation is completely lost. However, since older presbyopic patients may not have been able to focus at near for some years, it is possible that some patients may have either lost strength in their ciliary muscle or that some patients may have completely lost the ability to elicit an accommodative response in the ciliary muscle. It is possible, therefore, that some patients may not be suitable candidates for accommodation restoration procedures because of their inability to produce accommodative contractions of the ciliary muscle.

Using the above embodiments, patients may be screened pre-operatively or before presbyopia treatments commence to determine if they are suitable candidates for accommodation restoration procedures. This screening can save considerable expense and could improve patient outcomes post-operatively, by ensuring that only suitable candidates are selected for the accommodation restoration procedures.

Pre-operative electrical stimulation of accommodation or recording of electrical potentials from the ciliary muscle when patients make an effort to accommodate offers an opportunity to evaluate which patients may or may not be most suitable for accommodation restoration procedures. If strong electrical potentials can be recorded from the ciliary muscle pre-operatively in patients while they make an accommodative effort, this would provide evidence that the ciliary muscle is undergoing a strong contraction. If electrical stimulation of the ciliary muscle shows significant movements of the lens in the eye, such as a downward sag of the lens under the influence of gravity with an accommodative contraction of the ciliary muscle, this may indicate that the ciliary muscle is undergoing a strong contraction. Patients with strong ciliary muscle contractions would be ideal candidates for accommodation restoration procedures, while patients that show no accommodative contraction of the ciliary muscle would be poor candidates.

While the foregoing is directed to embodiments of the inventions, other and further embodiments of the inventions may be devised without departing from the basic scope thereof.

The invention claimed is:

1. An electrostimulation device, comprising:
 a device body with a circular shape and an outer circumference, the device body comprising a posterior surface and an anterior surface surrounding an aperture formed in the device body between the anterior surface and the posterior surface, the posterior surface being shaped to fit an eye, wherein the body is shaped as two conical frustums which reflect at a convergent plane;
 an inner ring electrode comprising an electrically-conductive material and formed on the posterior surface;
 an outer ring electrode comprising an electrically-conductive material and formed on the posterior surface; and
 an electrical stimulation source in electrical connection with the inner ring electrode and the outer ring electrode.

2. The electrostimulation device of claim 1, wherein the electrically conductive material comprises a biocompatible conductive material.

3. The electrostimulation device of claim 1, wherein the device body is composed of a non-conductive material.

4. The electrostimulation device of claim 1, wherein the electrical stimulation source comprises a battery formed on or in the device body.

5. The electrostimulation device of claim 1, further comprising a wireless connection for communication between the electrostimulation device and a computing device.

6. The electrostimulation device of claim 1, further comprising an intraocular lens.

* * * * *